(12) United States Patent
Jung et al.

(10) Patent No.: US 8,431,514 B2
(45) Date of Patent: *Apr. 30, 2013

(54) 4-CYANO-3-BENZOYLAMINO-N-PHENYL-BENZAMIDES FOR USE IN PEST CONTROL

(75) Inventors: Pierre Joseph Marcel Jung, Stein (CH); Christopher Richard Ayles Godfrey, Stein (CH); Ottmar Franz Hueter, Stein (CH); Peter Maienfisch, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/318,965

(22) PCT Filed: Apr. 14, 2010

(86) PCT No.: PCT/EP2010/054862
§ 371 (c)(1),
(2), (4) Date: Jan. 16, 2012

(87) PCT Pub. No.: WO2010/127926
PCT Pub. Date: Nov. 11, 2010

(65) Prior Publication Data
US 2012/0122975 A1   May 17, 2012

(30) Foreign Application Priority Data

May 6, 2009  (GB) .................................. 0907822.1
Dec. 18, 2009 (GB) .................................. 0922234.0

(51) Int. Cl.
C07C 255/58  (2006.01)
A01P 7/04    (2006.01)
A01P 7/00    (2006.01)
A01P 9/00    (2006.01)
A01P 5/00    (2006.01)

(52) U.S. Cl.
USPC ........... 504/310; 558/415; 558/420; 558/422; 564/139; 564/142; 564/163

(58) Field of Classification Search ........................ None
See application file for complete search history.

(56) References Cited

U.S. PATENT DOCUMENTS

2010/0056639 A1* 3/2010 Jung et al. ..................... 514/619

FOREIGN PATENT DOCUMENTS

| EP | 1714958 | 10/2006 |
| WO | 2008000438 | 1/2008 |
| WO | 2008074427 | 6/2008 |

* cited by examiner

*Primary Examiner* — Sreeni Padmanabhan
*Assistant Examiner* — Irina Neagu
(74) *Attorney, Agent, or Firm* — Brian D. McAlhaney

(57) ABSTRACT

The present invention relates to bis-amide derivatives of formula (I), to processes and intermediates for preparing them, to methods of using them to control insect, acarine, nematode and mollusc pests, and to insecticidal, acaricidal, nematicidal and molluscicidal compositions comprising them.

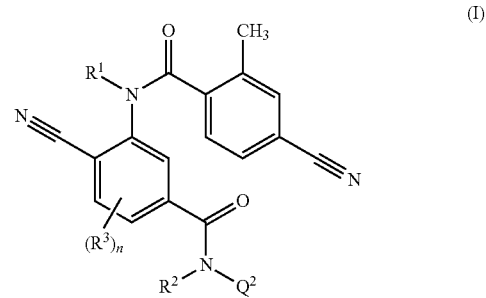

(I)

12 Claims, No Drawings

4-CYANO-3-BENZOYLAMINO-N-PHENYL-BENZAMIDES FOR USE IN PEST CONTROL

This application is a 371 of International Application No. PCT/EP2010/054862 filed Apr. 14, 2010, which claims priority to GB 0907822.1 filed May 6, 2009, and GB 0922234.0, filed Dec. 18, 2009, the contents of which are incorporated herein by reference.

The present invention relates to novel bis-amide derivatives having insecticidal activity, to processes and intermediates for preparing them, to methods of using them to control insect, acarine, nematode and mollusc pests and to insecticidal, acaricidal, nematicidal and molluscicidal compositions comprising them.

Compounds having insecticidal properties are disclosed in EP 1,714,958, JP 2006/306771, WO 2006/137376, EP 1,916,236, WO 2007/017075, WO 2008/000438, WO 2008/074427 and WO 2009/049845. There exists a need for alternative methods of control of pests. Preferably, new compounds may possess improved insecticidal properties, such as improved efficacy, improved selectivity, lower tendency to generate resistance or activity against a broader range of pests. Compounds may be more advantageously formulated or provide more efficient delivery and retention at sites of action, or may be more readily biodegradable.

It has now surprisingly been found that bis-amide derivatives having a particular substitution pattern on a terminal phenyl group have excellent insecticidal properties that are unexpectedly superior to previously disclosed compounds.

Accordingly, the present invention provides a compound of formula (I)

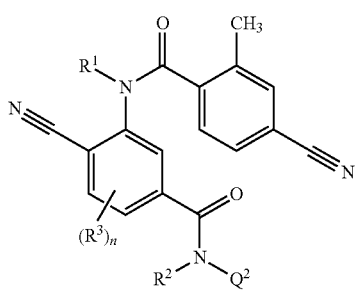

(I)

wherein
$R^1$ is hydrogen, $C_1$-$C_8$alkyl, $C_1$-$C_8$alkylcarbonyl, or $C_1$-$C_8$alkoxycarbonyl;
$R^2$ is hydrogen, $C_1$-$C_8$alkyl, $C_1$-$C_8$alkylcarbonyl, or $C_1$-$C_8$alkoxycarbonyl;
each $R^3$ is independently halogen;
n is 0, 1, 2 or 3;
$Q^2$ is a group of formula (II)

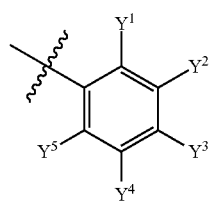

(II)

$Y^1$ and $Y^5$ are each independently selected from halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxy-$C_1$-$C_4$ alkyl, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl and $C_1$-$C_3$ haloalkylsulfonyl;
$Y^3$ is selected from $C_2$-$C_6$perfluoroalkyl, $C_2$-$C_6$perfluorocycloalkyl, hydroxy-$C_2$-$C_6$perfluoroalkyl, $C_1$-$C_4$ alkylcarbonyloxy-$C_2$-$C_6$perfluoroalkyl, $C_1$-$C_4$haloalkylcarbonyloxy-$C_2$-$C_6$perfluoroalkyl, $C_1$-$C_6$perfluoroalkylthio, $C_1$-$C_6$perfluoroalkylsulfinyl, $C_1$-$C_6$perfluoroalkylsulfonyl, arylcarbonyloxy-$C_2$-$C_6$perfluoroalkyl and arylcarbonyloxy-$C_2$-$C_6$perfluoroalkyl in which the aryl group may be substituted by one to five $R^4$ groups, which may be the same or different;
$Y^2$ and $Y^4$ are each independently selected from hydrogen, halogen and $C_1$-$C_4$ alkyl; and
$R^4$ is halogen, cyano, nitro, $C_1$-$C_4$ alkyl, $C_1$-$C_4$ haloalkyl, $C_1$-$C_4$ alkoxy or $C_1$-$C_4$ haloalkoxy;
or an agrochemically acceptable salt or N-oxides thereof.

The compounds of formula (I) may exist in different geometric or optical isomers (enantiomers and/or diastereoisomers) or tautomeric forms. This invention covers all such isomers and tautomers and mixtures thereof in all proportions as well as isotopic forms such as deuterated compounds.

Unless otherwise indicated, alkyl, on its own or as part of another group, such as alkoxy, alkylcarbonyl or alkoxycarbonyl, may be straight or branched chain and may contain from 1 to 8 carbon atoms, preferably 1 to 6, more preferably 1 to 4, and most preferably 1 to 3. Examples of alkyl include methyl, ethyl, n-propyl, iso-propyl, n-butyl, sec-butyl, iso-butyl and tert-butyl.

Hydroxyalkyl are alkyl groups, which are substituted by one or more hydroxy groups, and includes, for example, hydroxymethyl and 1,3-dihydroxypropyl.

Halogen means fluorine, chlorine, bromine or iodine.

Haloalkyl groups may contain one or more identical or different halogen atoms, and include, for example, difluoromethyl, trifluoromethyl, chlorodifluoromethyl, 2,2,2-trifluoroethyl and 2,2-difluoroethyl. Perfluoroalkyl groups are alkyl groups which are completely substituted with fluorine atoms and include, for example, trifluoromethyl, pentafluoroethyl, heptafluoroprop-2-yl and nonafluorobut-2-yl.

Hydroxyperfluoroalkyl groups are hydroxyalkyl groups which are substituted in every available position by a fluorine atom, and include, for example, hexafluoro-2-hydroxyprop-2-yl and octafluoro-2-hydroxybut-2-yl.

Cycloalkyl groups may be monocyclic or bicyclic and may preferably contain from 3 to 8 carbon atoms, more preferably 4 to 7, and most preferably 5 to 6, and include, for example, cyclopropyl, cyclobutyl, cyclohexyl and bicyclo[2.2.1]heptan-2-yl.

Perfluorocycloalkyl groups are cycloalkyl groups which are substituted in every available position by a fluorine atom, and include, for example, undecafluorocyclohexyl.

Aryl includes phenyl, naphthyl, anthracenyl, indenyl, phenanthrenyl and biphenyl, with phenyl being preferred.

Preferred values of $R^1$, $R^2$, $R^3$, n, $Q^2$, $Y^1$, $Y^2$, $Y^3$, $Y^4$, $Y^5$ and $R^4$ are, in any combination, as set out below.

Preferably, $R^1$ is hydrogen.
Preferably, $R^2$ is hydrogen.
Preferably, $R^3$ is fluoro.
In one preferred aspect, n is 0.
In another preferred aspect, n is 1. When n is 1, the $R^3$ group is preferably substituted in the 2-position of the phenyl ring.
Preferably, $Y^1$ is halogen, cyano, $C_1$-$C_4$ alkyl, $C_1$-$C_4$ alkoxy, $C_1$-$C_4$ alkoxy-$C_1$-$C_4$ alkyl or $C_1$-$C_3$ alkylthio. More preferably, $Y^1$ is fluoro, chloro, bromo, cyano, methyl, ethyl, methoxy, methylthio, or methoxymethyl. Most preferably, $Y^1$ is chloro, bromo, methyl, ethyl, or cyano.

Preferably, $Y^2$ is hydrogen, chloro, fluoro or methyl. More preferably, $Y^2$ is hydrogen or fluoro. Most preferably, $Y^2$ is hydrogen.

Preferably, $Y^3$ is $C_2$-$C_6$perfluoroalkyl, $C_2$-$C_6$perfluorocycloalkyl, hydroxy-$C_2$-$C_6$perfluoroalkyl, arylcarbonyloxy-$C_2$-$C_6$perfluoroalkyl, or arylcarbonyloxy-$C_2$-$C_6$perfluoroalkyl in which the aryl group may be substituted by one to five $R^4$ groups, which may be the same or different. More preferably, $Y^3$ is heptafluoropropyl, nonafluorobutyl, undecafluorocyclohexyl, heptafluoropropylthio, heptafluoropropylsulfinyl, or heptafluoropropylsulfonyl. Yet more preferably, $Y^3$ is heptafluoroprop-1-yl, heptafluoroprop-2-yl, nonafluorobut-2-yl or undecafluorocyclohexyl. Most preferably, $Y^3$ is heptafluoroprop-2-yl, nonafluorobut-2-yl or undecafluorocyclohexyl.

Preferably, $Y^4$ is hydrogen, chloro, fluoro or methyl. More preferably, $Y^4$ is hydrogen or fluoro. Most preferably, $Y^4$ is hydrogen.

Preferably, $Y^5$ is halogen, cyano, $C_1$-$C_4$ alkyl, $C_1$-$C_4$ alkoxy, $C_1$-$C_4$ alkoxy-$C_1$-$C_4$ alkyl or $C_1$-$C_3$ alkylthio. More preferably, $Y^5$ is fluoro, chloro, bromo, cyano, methyl, ethyl, methoxy, methylthio, or methoxymethyl. Most preferably, $Y^5$ is chloro, bromo, methyl, ethyl, or cyano.

Preferably, $R^4$ is chloro, fluoro, cyano, nitro, methyl, ethyl, trifluoromethyl, methoxy, or trifluoromethoxy.

Most preferably, $Q^2$ is selected from
2-bromo-6-chloro-4-(hexafluoro-2-benzoyloxyprop-2-yl) phenyl,
2-bromo-6-chloro-4-(hexafluoro-2-hydroxyprop-2-yl)phenyl,
2-bromo-6-chloro-4-(nonafluorobut-2-yl)phenyl,
2-bromo-6-ethyl-4-(nonafluorobut-2-yl)phenyl,
2-chloro-6-cyano-4-(nonafluorobut-2-yl)phenyl,
2-chloro-6-methylthio-4-(nonafluorobut-2-yl)phenyl,
2,6-dibromo-4-(heptafluoroprop-2-yl)phenyl,
2,6-dibromo-4-(nonafluorobut-2-yl)phenyl,
2,6-dichloro-3-fluoro-4-(heptafluoroprop-2-yl)phenyl,
2,6-dichloro-4-(nonafluorobut-2-yl)phenyl,
2,6-dimethyl-4-(nonafluorobut-2-yl)phenyl,
2,6-dimethyl-4-(undecafluorocyclohexyl)phenyl,
2-ethyl-6-methyl-4-(nonafluorobut-2-yl)phenyl,
2-ethyl-6-methyl-4-(octafluoro-2-hydroxybut-2-yl)phenyl,
2-methoxymethyl-6-methyl-4-(nonafluorobut-2-yl)phenyl, and
2-methoxy-6-methyl-4-(nonafluorobut-2-yl)phenyl.

In a preferred embodiment of the invention,
$R^1$ and $R^2$ are both hydrogen;
n is 0 or 1;
$Y^1$ is halogen, cyano, $C_1$-$C_4$ alkyl, $C_1$-$C_4$ alkoxy, $C_1$-$C_4$ alkoxy-$C_1$-$C_4$ alkyl or $C_1$-$C_3$ alkylthio;
$Y^2$ and $Y^4$ are both hydrogen;
$Y^3$ is heptafluoropropyl, nonafluorobutyl, undecafluorocyclohexyl, heptafluoropropylthio, heptafluoropropylsulfinyl, or heptafluoropropylsulfonyl; and
$Y^5$ is halogen, cyano, $C_1$-$C_4$ alkyl, $C_1$-$C_4$ alkoxy, $C_1$-$C_4$ alkoxy-$C_1$-$C_4$ alkyl or $C_1$-$C_3$ alkylthio.

In a more preferred embodiment of the invention,
$R^1$ and $R^2$ are both hydrogen;
n is 0 or 1;
$Y^1$ is fluoro, chloro, bromo, cyano, methyl, ethyl, methoxy, methylthio, or methoxymethyl;
$Y^2$ and $Y^4$ are both hydrogen;
$Y^3$ is heptafluoroprop-1-yl, heptafluoroprop-2-yl, nonafluorobut-2-yl or undecafluorocyclohexyl; and $Y^5$ is fluoro, chloro, bromo, cyano, methyl, ethyl, methoxy, methylthio, or methoxymethyl.

In a yet more preferred embodiment of the invention,
$R^1$ and $R^2$ are both hydrogen;
n is 0 or 1;
$R^3$ is fluoro;
Y is chloro, bromo, methyl, ethyl, or cyano;
$Y^2$ and $Y^4$ are both hydrogen;
$Y^3$ is heptafluoroprop-2-yl, nonafluorobut-2-yl or undecafluorocyclohexyl; and
$Y^5$ is chloro, bromo, methyl, ethyl, or cyano.

In a first preferred aspect of the invention,
$R^1$ and $R^2$ are both hydrogen;
n is 1;
$R^3$ is 2-fluoro; and
$Q^2$ is selected from
2-bromo-6-chloro-4-(hexafluoro-2-benzoyloxyprop-2-yl) phenyl,
2-bromo-6-chloro-4-(hexafluoro-2-hydroxyprop-2-yl)phenyl,
2-bromo-6-chloro-4-(nonafluorobut-2-yl)phenyl,
2-bromo-6-ethyl-4-(nonafluorobut-2-yl)phenyl,
2-chloro-6-cyano-4-(nonafluorobut-2-yl)phenyl,
2-chloro-6-methylthio-4-(nonafluorobut-2-yl)phenyl,
2,6-dibromo-4-(heptafluoroprop-2-yl)phenyl,
2,6-dibromo-4-(nonafluorobut-2-yl)phenyl,
2,6-dichloro-3-fluoro-4-(heptafluoroprop-2-yl)phenyl,
2,6-dichloro-4-(nonafluorobut-2-yl)phenyl,
2,6-dimethyl-4-(nonafluorobut-2-yl)phenyl,
2,6-dimethyl-4-(undecafluorocyclohexyl)phenyl,
2-ethyl-6-methyl-4-(nonafluorobut-2-yl)phenyl,
2-ethyl-6-methyl-4-(octafluoro-2-hydroxybut-2-yl)phenyl,
2-methoxymethyl-6-methyl-4-(nonafluorobut-2-yl)phenyl, and
2-methoxy-6-methyl-4-(nonafluorobut-2-yl)phenyl.

In a second preferred aspect of the invention,
$R^1$ and $R^2$ are both hydrogen;
n is 0; and
$Q^2$ is selected from
2-bromo-6-chloro-4-(hexafluoro-2-benzoyloxyprop-2-yl) phenyl,
2-bromo-6-chloro-4-(hexafluoro-2-hydroxyprop-2-yl)phenyl,
2-bromo-6-chloro-4-(nonafluorobut-2-yl)phenyl,
2-bromo-6-ethyl-4-(nonafluorobut-2-yl)phenyl,
2-chloro-6-cyano-4-(nonafluorobut-2-yl)phenyl,
2-chloro-6-methylthio-4-(nonafluorobut-2-yl)phenyl,
2,6-dibromo-4-(heptafluoroprop-2-yl)phenyl,
2,6-dibromo-4-(nonafluorobut-2-yl)phenyl,
2,6-dichloro-3-fluoro-4-(heptafluoroprop-2-yl)phenyl,
2,6-dichloro-4-(nonafluorobut-2-yl)phenyl,
2,6-dimethyl-4-(nonafluorobut-2-yl)phenyl,
2,6-dimethyl-4-(undecafluorocyclohexyl)phenyl,
2-ethyl-6-methyl-4-(nonafluorobut-2-yl)phenyl,
2-ethyl-6-methyl-4-(octafluoro-2-hydroxybut-2-yl)phenyl,
2-methoxymethyl-6-methyl-4-(nonafluorobut-2-yl)phenyl, and
2-methoxy-6-methyl-4-(nonafluorobut-2-yl)phenyl.

Most preferred compounds of formula (I) are selected from
4-cyano-3-(4'-cyano-2'-methyl-benzoylamino)-N-[2,6-dibromo-4-(1,2,2,3,3,3-hexafluoro-1-trifluoromethyl-propyl)-phenyl]-benzamide;
4-cyano-3-(4'-cyano-2'-methylbenzoylamino)-N-[2,6-dichloro-4-(1,2,2,3,3,3-hexafluoro-1-trifluoromethylpropyl)phenyl]-2-fluorobenzamide;

N-[2-chloro-6-cyano-4-(1,2,2,3,3,3-hexafluoro-1-trifluoromethylpropyl)phenyl]-4-cyano-3-(4'-cyano-2'-methylbenzoylamino)benzamide;

N-[2-bromo-6-chloro-4-[1,1,1,3,3,3-hexafluoropropan-2-ol)phenyl]-4-cyano-3-(4'-cyano-2'-methylbenzoylamino)benzamide;

N-[2-bromo-6-chloro-4-(1,2,2,3,3,3-hexafluoro-1-trifluoromethylpropyl)phenyl]-4-cyano-3-(4'-cyano-2'-methylbenzoylamino)benzamide;

4-cyano-3-(4'-cyano-2'-methylbenzoylamino)-N-[2,6-dichloro-4-(1,2,2,3,3,3-hexafluoro-1-trifluoromethylpropyl)phenyl]benzamide;

4-cyano-3-(4'-cyano-2'-methylbenzoylamino)-N-[2,6-dichloro-4-(1,2,2,2-tetrafluoro-1-trifluoromethylethyl)phenyl]benzamide; and 4-cyano-3-(4'-cyano-2'-methylbenzoylamino)-N-[2-bromo-6-chloro-4-(1,2,2,2-tetrafluoro-1-trifluoromethylethyl)phenyl]benzamide.

The compounds of the invention may be made by a variety of methods, for example, the methods disclosed in WO 2008/074427.

1) Compounds of formula (I) may be made by treatment of compounds of formula (V), wherein R is OH, $C_1$-$C_6$ alkoxy, Cl, F or Br with an amine of formula $NHR^2Q^2$.

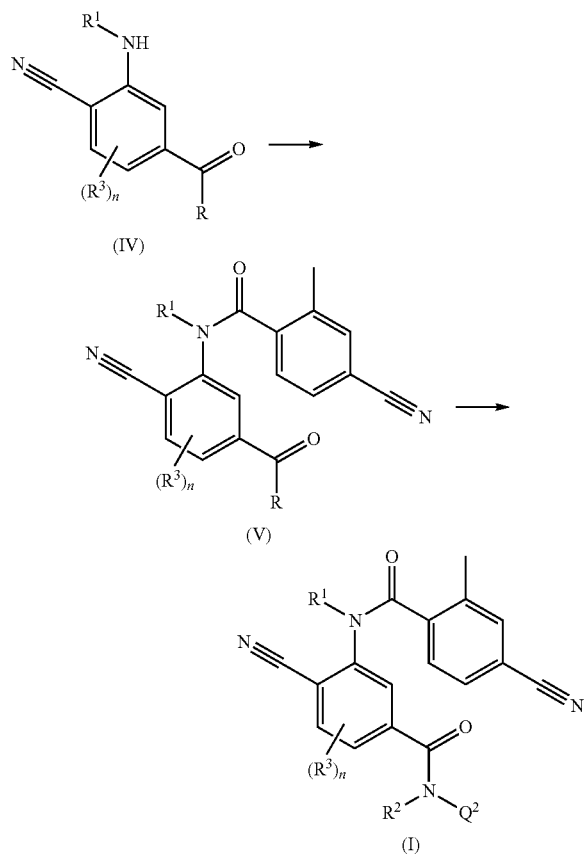

When R is OH such reactions may be carried out in the presence of a coupling reagent, such as DCC(N,N'-dicyclohexylcarbodiimide), EDC (1-ethyl-3-[3-dimethylamino-propyl]-carbodiimide hydrochloride) or BOP-Cl (bis(2-oxo-3-oxazolidinyl)phosphonic chloride), in the presence of a base, such as pyridine, triethylamine, 4-(dimethylamino)-pyridine or diisopropylethylamine, and optionally in the presence of a nucleophilic catalyst, such as hydroxybenzotriazole. When R is Cl, such reactions may be carried out under basic conditions, for example in the presence of pyridine, triethylamine, 4-(dimethylamino)-pyridine or diisopropylethylamine, optionally in the presence of a nucleophilic catalyst. Alternatively, the reaction may be conducted in a biphasic system comprising an organic solvent, preferably ethyl acetate, and an aqueous solvent, preferably a solution of sodium hydrogen carbonate. When R is $C_1$-$C_6$ alkoxy the ester may be converted directly to the amide by heating the ester and amine together in a thermal process.

2) Acid halides of formula (V), wherein R is Cl, F or Br, may be made from carboxylic acids of formula (V), wherein R is OH, under standard conditions, such as treatment with thionyl chloride or oxalyl chloride.

3) Carboxylic acids of formula (V), wherein R is OH, may be formed from esters of formula (V), wherein R is $C_1$-$C_6$ alkoxy by treatment of the ester with an alkali hydroxide, such as sodium hydroxide, in a solvent, such as ethanol and/or water.

4) Esters of formula (V), wherein R is $C_1$-$C_6$ alkoxy, may be made by treatment of compounds of formula (IV), wherein R is $C_1$-$C_6$ alkoxy, by acylation with the 2-methyl-4-cyanobenzoic acid or an acid halide derivate from 2-methyl-4-cyanobenzoic acid, wherein the halide is Cl, F or Br, under standard conditions as described in 1).

5) Acids of formula (V), wherein R is $C_1$-$C_6$ alkoxy, may be made by treatment of compounds of formula (IV), wherein R is OH, by acylation with 2-methyl-4-cyanobenzoic acid or an acid halide derived from 2-methyl-4-cyanobenzoic acid, wherein the halide is Cl, F or Br, under standard conditions as described in 1).

6) Compounds of formula (IV), wherein R is $C_1$-$C_6$ alkoxy, may be made from compounds of formula (VI) by sequential treatment with an alcohol R—OH under acidic conditions and then formation of the N—$R^1$ bond.

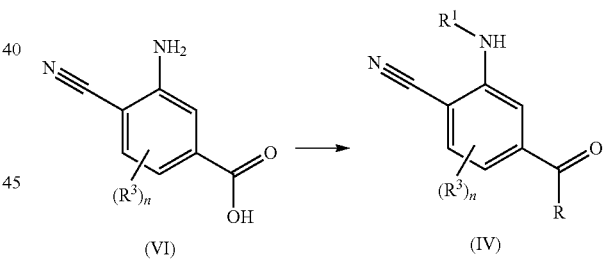

For example, reactions based on oxidized versions of the alcohols such as the corresponding aldehydes and ketones or based on more activated analogues of the alcohols such as the corresponding halides or sulfonates may be used. Alternatively, reductive amination may be achieved by treatment of the amine with an aldehyde or ketone and a reducing agent such as sodium cyanoborohydride or sodium borohydride. Alternatively, alkylation may be achieved by treating the amine with an alkylating agent such as an alkyl halide, optionally in the presence of a base. Alternatively, arylation may be achieved by treatment of the amine with an aryl halide or sulfonate in the presence of a suitable catalyst/ligand system, often a palladium (0) complex. Compounds of formula (VI) and alcohols of formula R—OH are either known compounds or may be made by known methods known to a person skilled in the art.

7) Alternatively, compounds of formula (IV), wherein R is $C_1$-$C_6$ alkoxy, may be made from a compound of formula (VII), wherein R is $C_1$-$C_6$ alkoxy and LG is a leaving group, such as fluoro, chloro or sulfonate, via nucleophilic displacement of the leaving group by an amine of formula $R^1$—$NH_2$.

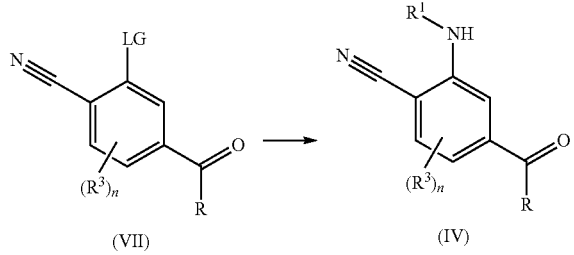

Compounds of formula (VII) and amines of formula $R^1$—$NH_2$ are either known compounds or may be made by known methods known to a person skilled in the art.

8) Alternatively, compounds of formula (I), may be made by the treatment of compounds of formula (IX) with the 2-methyl-4-cyanobenzoic acid or an acid halide derivate from 2-methyl-4-cyanobenzoic acid, wherein the halide is Cl, F or Br, under standard conditions as described in 1).

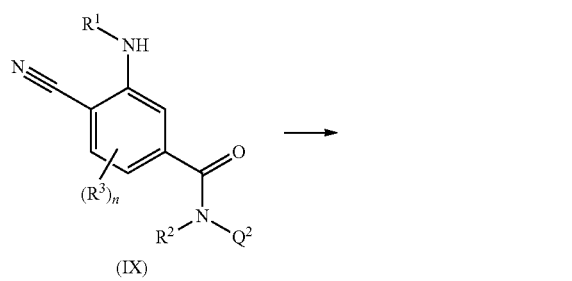

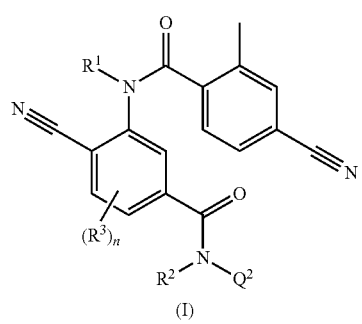

9) Compounds of formula (IX), may be formed from compounds of formula (VIII), wherein P is a suitable protecting group and R is OH, $C_1$ or $C_1$-$C_6$ alkoxy, by amide bond formation with an amine of formula $NHR^2Q^2$ under standard conditions as described in 1), followed by removal of the protecting group P under standard conditions.

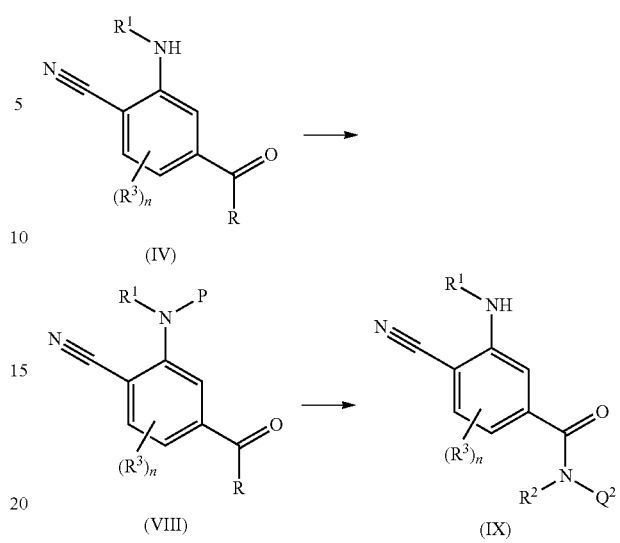

10) Compounds of formula (VIII), wherein R is OH or $C_1$-$C_6$ alkoxy, may be made by the protection of the amine functionality in compounds of formula (IV), wherein R is OH or $C_1$-$C_6$ alkoxy. Suitable protecting groups include carbamates, such as tert-butyloxycarbonyl, allyloxycarbonyl and benzyloxycarbonyl, trialkylsilyl groups, such as tert-butyldimethylsilyl, and acyl groups, such as acetyl. The formation and removal of such groups is widely reported in the literature and is known to a person skilled in the art.

11) For compounds of formula (VIII) and compounds of formula (IV), the esters, wherein R is $C_1$-$C_6$ alkoxy, may be hydrolysed to the acids, wherein R is OH, by treatment with an alkali hydroxide, such as sodium hydroxide, in a solvent, such as ethanol. The acids may be converted to the acid chlorides, wherein R is Cl, by treatment with thionyl chloride or oxalyl chloride as described in 2) and 3).

12) Alternatively, the compounds of formula (IV), wherein R is OH, Cl, F, Br or $C_1$-$C_6$ alkoxy, may be converted directly to compounds of formula (IX) by amide bond formation with an amine of formula $NHR^2Q^2$ under standard conditions as described in 1).

13) Alternatively, compounds of formula (IX), may be made from compounds of formula (XI), wherein LG is a leaving group such as iodo, bromo, chloro or sulfonate, by displacement of the leaving group with a compound of formula $R^1$—$NH_2$ or other imine analogue with a metal catalyst, followed by hydrolysis. See for example: Chemical Communications (2009), (14), 1891-1893 or Journal of Organic Chemistry (2000), 65(8), 2612-2614. Compounds of formula (X) and formula (IV) are either known compounds or may be made by methods known to a person skilled in the art.

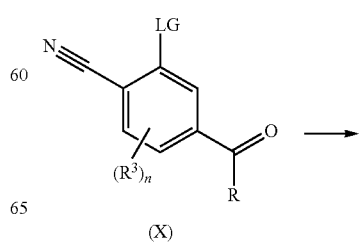

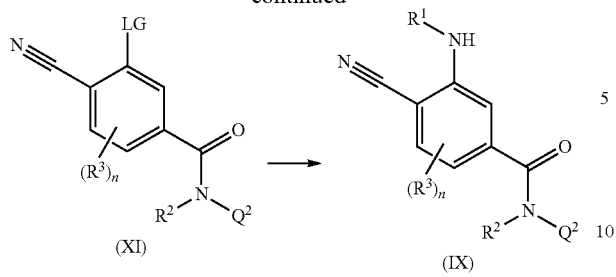

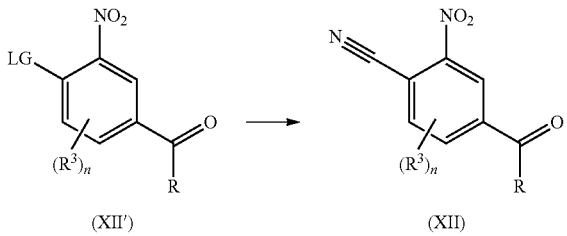

14) Alternatively, compounds of formula (IX) may be prepared by formation of a N—R$^1$ bond in a compound of formula (IX') using the methods as described in 6).

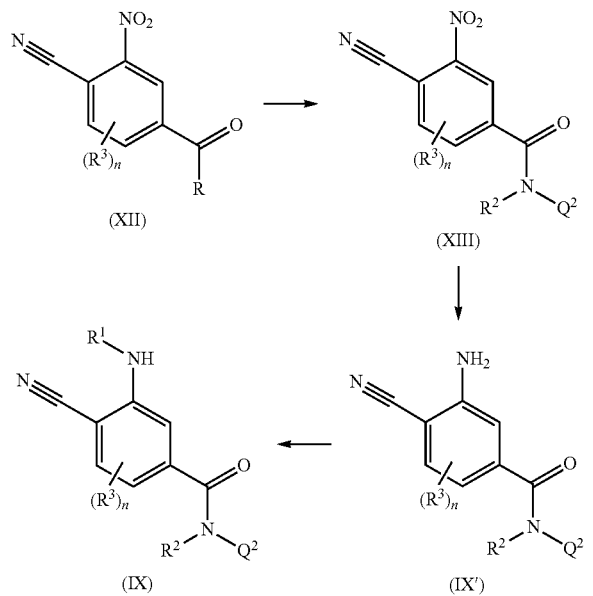

15) Compounds of formula (IX'), may be made by the reduction of a nitro compound of formula (XIII), such as by treatment with tin chloride under acidic conditions, or hydrogenation catalysed by a noble metal such as palladium on carbon.

16) Compounds of formula (XIII) may be derived from compounds of formula (XII), wherein R is OH, Cl, or $C_1$-$C_6$ alkoxy, via acylation with an amine of formula NHR$^2$Q$^2$ under the standard conditions as described in 1).

17) For compounds of formula (XII), the esters, wherein R is $C_1$-$C_6$ alkoxy, may be hydrolysed to the acids, wherein R is OH, by treatment with an alkali hydroxide, such as sodium hydroxide, in a solvent, such as ethanol as described in 3). The acids may be converted to the acid chlorides, wherein R is Cl, by treatment with thionyl chloride or oxalyl chloride as described in 2). Compounds of formula (XII) are either known or may be made by methods known to a person skilled in the art.

18) Compounds of formula (XII) can be made from a compound of formula (XII') wherein LG is halogen, such as fluoride or chloride, by reaction with a cyanide salt, such as potassium cyanide, optionally in the presence of a base, such as potassium carbonate.

The displacement of a halogen with cyanide can also be carried out on intermediates of formula (XIII) wherein the cyano group is replaced by a leaving group such as fluoride or chloride. In both instances the presence of the nitro group facilitates the displacement of the leaving group by the cyanide ion.

19) Compounds of formula (XII) can be made from a compound of formula (XII') wherein LG is an amine, by reaction with a cyanide salt, such as copper cyanide, via a diazotisation reaction. The displacement of an amine with cyanide can also be carried out on intermediates of formula (XIII) wherein the cyano group is replace by a leaving group such as amine.

20) Compounds of formula (XII) can be made from a compound of formula (XII') wherein LG is an halogen such as Br or I, by reaction with a cyanide salt, such as copper cyanide or Zinc cyanide via a metal catalyse reaction such as palladium catalyst. See for example: Synthetic Communications (1994), 24(6), 887-90). The displacement of the halogen with cyanide can also be carried out on intermediates of formula (XIII) wherein the cyano group is replaced by a leaving group such as bromide or iodide.

21) Compounds of formula (I), (V), (IV), (VI), (VII), (IX), (VIII) can be made from compounds of formula (I), (V), (IV), (VI), (VII), (IX), (VIII) wherein the cyano group is replaced by a leaving group such as bromide or iodide by the same reaction described in 20).

The compounds of formula (I) can be used to control infestations of insect pests such as *Lepidoptera, Diptera, Hemiptera, Thysanoptera, Orthoptera, Dictyoptera, Coleoptera, Siphonaptera, Hymenoptera* and *Isoptera* and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example Coptotermesformosanus, *Reticulitermes flavipes, R. speratu, R. virginicus, R. hesperus*, and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, sulfoxaflor, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;
o) Indoxacarb;
p) Chlorfenapyr;
q) Pymetrozine;
r) Spirotetramat, spirodiclofen or spiromesifen;
s) Diamides, such as flubendiamide, chlorantraniliprole or cyantraniliprole;
t) Sulfoxaflor; or
u) Metaflumizone.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, c-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC3 82042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N([methyl(methyl-thioethylideneaminooxycarbonyl)amino]thio)-3-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrroInitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

PREPARATION EXAMPLES

The following abbreviations were used in this section: s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; M.p.=melting point; RT=retention time, [M+H]$^+$= molecular mass of the molecular cation, [M−H]$^-$=molecular mass of the molecular anion.
The following LC-MS methods were used to characterize the compounds:

| Method 1 | |
| --- | --- |
| MS | ZQ Mass Spectrometer from Waters (Single quadrupole mass spectrometer), ionization method: electrospray, polarity: positive ionization, capillary (kV) 3.00, cone (V) 30.00, |

-continued

Method 1

| | |
|---|---|
| | source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, quaternary pump, heated column compartment and diode-array detector. Column: Phenomenex Gemini C18, 3 μm particle size, 110 Angstrom, 30 × 3 mm, temperature (° C.) 60, DAD wavelength range (nm): 200 to 500, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method 2

| | |
|---|---|
| MS | ZQ Mass Spectrometer from Waters (Single quadrupole mass spectrometer), ionization method: electrospray, polarity: positive or negative ionization, capillary (kV) 3.10, cone (V) 30.00, source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, binary pump, heated column compartment and diode-array detector. Column: Phenomenex Gemini C18, 3 μm particle size, 110 Angstrom, 30 × 3 mm, temperature (° C.) 60, DAD wavelength range (nm): 200 to 500, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method 3

| | |
|---|---|
| MS | ZQ Mass Spectrometer from Waters (Single quadrupole mass spectrometer), Instrument Parameter: Ionisation method: Electrospray, Polarity: positive ions Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400, Mass range: 150 to 1000 Da |
| LC | HP 1100 HPLC from Agilent: solvent degasser, quaternary pump (ZCQ)/binary pump (ZDQ), heated column compartment and diode-array detector. Column: Phenomenex Gemini C18, 3 μm particle size, 110 Angström, 30 × 3 mm, Temp: 60° C., DAD Wavelength range (nm): 200 to 500, Solvent Gradient: A = water + 0.05% HCOOH, B = Acetonitril/Methanol (4:1, v:v) + 0.04% HCOOH |

| Time | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method 4

| | |
|---|---|
| MS | ZMD Mass Spectrometer from Micromass (Single quadrupole mass spectrometer), ionization method: electrospray, polarity: positive ionization, capillary (kV) 3.80, cone (V) 30.00, source temperature (° C.) 80, desolvation temperature (° C.) 200, desolvation gas flow (L/Hr) 600, mass range: 150 to 1000 Da. |
| LC | HP 1100 HPLC from Agilent: solvent degasser, binary pump, heated column compartment and wavelength detector. Column: Phenomenex Gemini C18, 3 μm particle size, 110 Angstrom, 30 × 3 mm, temperature (° C.) 60, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method 5

| | |
|---|---|
| MS | ZQ Mass Spectrometer from Waters (Single quadrupole mass spectrometer) Instrument Parameter: Ionisation method: Electrospray, Polarity: positive (or negative) ions, Capillary (kV) 3.00, Cone (V) 30.00 (AIDA: 45 V), Extractor (V) 2.00, Source Temperature (° C.) 100, Desolvation Temperature (° C.) 250, Cone Gas Flow (L/Hr) 50, Desolvation Gas Flow (L/Hr) 400, Mass range: 100 to 900 Da |
| LC | HP 1100 HPLC from Agilent: solvent degasser, quaternary pump (ZCQ)/binary pump (ZDQ), heated column compartment and diode-array detector. Column: Phenomenex Gemini C18, 3 μm particle size, 110 Angström, 30 × 3 mm, Temp: 60° C., DAD Wavelength range (nm): 200 to 500, Solvent Gradient: A = water + 0.05% HCOOH, B = Acetonitril/Methanol (4:1, v:v) + 0.04% HCOOH |

| Time | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method D

| | |
|---|---|
| MS | ZQ Mass Spectrometer from Waters (Single quadrupole mass spectrometer), ionization method: electrospray, polarity: positive ionization, capillary (kV) 3.00, cone (V) 30.00, source temperature (° C.) 150, desolvation temperature (° C.) 350, cone gas flow (L/Hr) 50, desolvation gas flow (L/Hr) 400, mass range: 150 to 1000 Da. |
| LC | HP 1100 HPLC from Agilent: solvent degasser, quaternary pump, heated column compartment and diode-array detector. Column: Phenomenex Gemini C18, 3 μm particle size, 110 Angstrom, 30 × 3 mm, temperature (° C.) 60, DAD wavelength range (nm): 200 to 500, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

1. Preparation of Intermediates

Example 1.1

N-[2-bromo-6-chloro-4-(1,2,2,3,3,3-hexafluoro-1-trifluoromethylpropyl)-phenyl]-4-cyano-3-nitrobenzamide

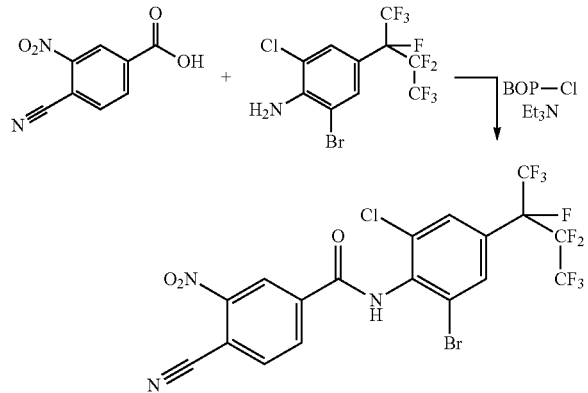

To a suspension of 2-bromo-6-chloro-4-(1,2,2,3,3,3-hexafluoro-1-trifluoromethyl-propyl)phenylamine (Example 3.3) (70 g, 165 mmol) in 1,2-dichloroethane (660 ml) was added triethylamine (50.09 g, 495 mmol), followed by 4-cyano-3-nitrobenzoic acid (made as in WO 2008/074427) (63.4 g, 330 mmol) and bis(2-oxo-3-oxazolidinyl)phosphonic chloride ("BOP-Cl") (84 g, 330 mmol). The reaction mixture was stirred at 90° C. for 6 hours. The reaction was quenched by addition of aqueous hydrochloric acid (1M) (500 ml) and the phases were separated. The organic phase was washed with saturated aqueous sodium hydrogen carbonate and brine. The aqueous phase was extracted twice with 1,2-dichloroethane. The combined organic extracts were dried over sodium sulfate and concentrated. The residue was purified by column chromatography on silica gel (eluent: cyclohexane/ethyl acetate 7:3) to give N-[2-bromo-6-chloro-4-(1,2,2,3,3,3-hexafluoro-1-trifluoromethylpropyl)phenyl]-4-cyano-3-nitrobenzamide (89 g, 90% yield). $^1$H NMR (400 MHz, CDCl$_3$): 8.89 (s, 1H), 8.40 (d, 1H), 8.12 (d, 1H), 7.88 (m, 2H), 7.72 (s, 1H).

Example 1.2

4-cyano-N-[2,6-dichloro-3-fluoro-4-(1,2,2,2-tetrafluoro-1-trifluoromethyl-ethyl)phenyl]-3-nitrobenzamide

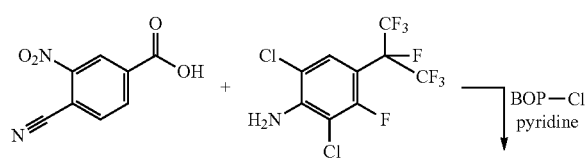

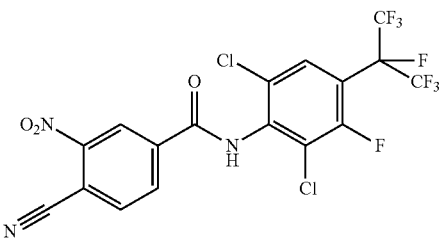

To a solution of 2,6-dichloro-3-fluoro-4-(1,2,2,2-tetrafluoro-1-trifluoromethylethyl)-phenylamine (Example 3.2) (3.48 g, 10 mmol) and 4-cyano-3-nitrobenzoic acid (made as in WO 2008/074427) (3.84 g, 20 mmol) in dichloromethane (40 ml) was added pyridine (4.17 ml, 30 mmol) and bis(2-oxo-3-oxazolidinyl)phosphonic chloride ("BOP-Cl") (5.09 g, 20 mmol). The reaction mixture was heated to reflux for 6 hours. The reaction mixture was cooled to ambient temperature and quenched by addition of aqueous hydrochloric acid (1N) (50 ml). The mixture was then extracted three times with dichloromethane. The combined organic extracts were washed with saturated aqueous sodium hydrogen carbonate, dried over sodium sulfate and concentrated. The residue was purified by column chromatography on silica gel (eluent: cyclohexane/ethyl acetate 7:3) to give 4-cyano-N-[2,6-dichloro-3-fluoro-4-(1,2,2,2-tetrafluoro-1-trifluoromethyl-ethyl)phenyl]-3-nitrobenzamide (4.76 g, 91% yield). LC-MS (Method 2): RT=2.08, [M–H]$^-$=520.

Similarly, 4-cyano-N-[2,6-dichloro-4-(1,2,2,3,3,3-hexafluoro-1-trifluoromethyl-propyl)phenyl]-2,3-difluorobenzamide was made from 2,6-dichloro-4-(1,2,2,3,3,3-hexafluoro-1-trifluoromethylpropyl)phenylamine (Example 3.2) and 4-cyano-2,3-difluoro-benzoic acid (made as in WO 2008/074427). LC-MS (Method 2): RT=2.11, [M–H]$^-$=543.

Similarly, 4-cyano-N-[2-ethyl-6-methyl-4-(2,2,3,3,3-pentafluoro-1-hydroxy-1-trifluoromethylpropyl)phenyl]-3-nitrobenzamide was made from 2-(4-amino-3-ethyl-5-methylphenyl)-1,1,1,3,3,4,4,4-octafluorobutan-2-ol (Example 3.5) and 4-cyano-3-nitro-benzoic acid (made as in WO 2008/074427). $^1$H NMR (400 MHz, CDCl$_3$): 8.85 (s, 1H), 8.37 (dd, 1H), 8.09 (d, 1H), 7.78 (s, 1H), 7.52 (s, 2H), 3.82 (bs, 1H), 2.64 (q, 2H), 2.30 (s, 3H), 1.20 (t, 3H).

Similarly, benzoic acid 1-[3-bromo-5-chloro-4-(4-cyano-3-nitrobenzoylamino)-phenyl]-2,2,2-trifluoro-1-trifluoromethylethyl ester was made from benzoic acid 1-(4-amino-3-bromo-5-chlorophenyl)-2,2,2-trifluoro-1-trifluoromethylethyl ester (Example 3.8) and 4-cyano-3-nitrobenzoic acid (made as in WO 2008/074427). $^1$H NMR (400 MHz, CDCl$_3$): 8.85 (s, 1H), 8.37 (d, 1H), 8.12 (m, 3H), 77.8-7.65 (m, 3H), 7.57 (m, 3H).

Similarly, N-[2-bromo-6-chloro-4-(1,2,2,2-tetrafluoro-1-trifluoromethylethyl)-phenyl]-4-cyano-3-nitrobenzamide was made from 2-bromo-6-chloro-4-(1,2,2,2-tetrafluoro-1-trifluoromethylethyl)phenylamine (Example 3.3) and 4-cyano-3-nitrobenzoic acid (made as in WO 2008/074427). The compound was used without extra purification after work up.

Example 1.3

4-cyano-N-[2,6-dibromo-4-(1,2,2,3,3,3-hexafluoro-1-trifluoromethylpropyl)-phenyl]-3-nitrobenzamide

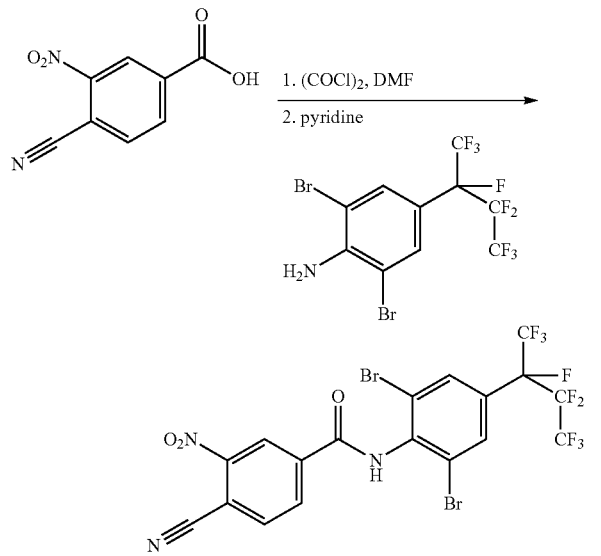

To a suspension of 4-cyano-3-nitrobenzoic acid (prepared as described in WO 2008/074427) (30 g, 156 mmol) in dichloromethane (150 ml) was added oxalyl chloride (15.88 ml, 187 mmol) at ambient temperature, followed by N,N-dimethylformamide ("DMF") (0.2 ml). The reaction mixture was stirred for 30 minutes at ambient temperature and then heated to reflux for 30 minutes. The reaction mixture was allowed to cool to ambient temperature, concentrated and the residue was suspended in tetrahydrofuran (150 ml). A solution of 2,6-dibromo-4-(1,2,2,3,3,3-hexafluoro-1-trifluoromethylpropyl)-phenylamine (Example 3.2) (55 g, 117.3 mmol) in a mixture of tetrahydrofuran (150 ml) and pyridine (12.57 ml, 156.4 mmol) was cooled to 0° C. and the solution of 4-cyano-3-nitrobenzoyl chloride was added. The reaction mixture was stirred at ambient temperature for 12 hours. Satruated aqueous sodium hydrogen carbonate (300 ml) was added and the organic phase extracted twice with ethyl acetate (2×200 ml). The combined organic extracts were dried over sodium sulfate and concentrated. The residue was purified by column chromatography on silica gel (eluent: cyclohexane/ethyl acetate 4:1) to give 4-cyano-N-[2,6-dibromo-4-(1,2,2,3,3,3-hexafluoro-1-trifluoromethylpropyl)phenyl]-3-nitrobenzamide (28 g, 37% yield). LC-MS (Method 2): RT=2.24, $[M-H]^-=642$.

Similarly, 4-cyano-N-[2-methoxy-6-methyl-4-(1,2,2,3,3,3-hexafluoro-1-trifluoro-methylpropyl)phenyl]-3-nitrobenzamide was made from 4-(1,2,2,3,3,3-hexafluoro-1-trifluoromethylpropyl)-2-methoxy-6-methylphenylamine (Example 3.1) and 4-cyano-3-nitro-benzoic acid (prepared as described in WO 2008/074427).

LC-MS (Method 2): RT=2.04, $[M-H]^-=528$.

Similarly, 4-cyano-N-[2,6-dichloro-4-(1,2,2,3,3,3-hexafluoro-1-trifluoromethyl-propyl)phenyl]-3-nitrobenzamide was made from 2,6-dichloro-4-(1,2,2,3,3,3-hexafluoro-1-trifluoromethylpropyl)phenylamine (Example 3.2) and 4-cyano-3-nitrobenzoic acid (prepared as described in WO 2008/074427). LC-MS (Method 2): RT=2.08, $[M-H]^-=553$.

Similarly, 4-cyano-N-[2,6-dichloro-4-(1,2,2,2-tetrafluoro-1-trifluoromethylethyl)-phenyl]-3-nitrobenzamide was made from 2,6-dichloro-4-(1,2,2,2-tetrafluoro-1-trifluoro-methylethyl)phenylamine (prepared as described in WO 2009/030457) and 4-cyano-3-nitrobenzoic acid (prepared as described in WO 2008/074427).

LC-MS (Method 3): RT=2.06, $[M-H]^-=502$ $(M-H^+)$.

Example 1.4

N-[2-bromo-6-chloro-4-(1,2,2,3,3,3-hexafluoro-1-trifluoromethylpropyl)-phenyl]-4-cyano-2,3-difluorobenzamide

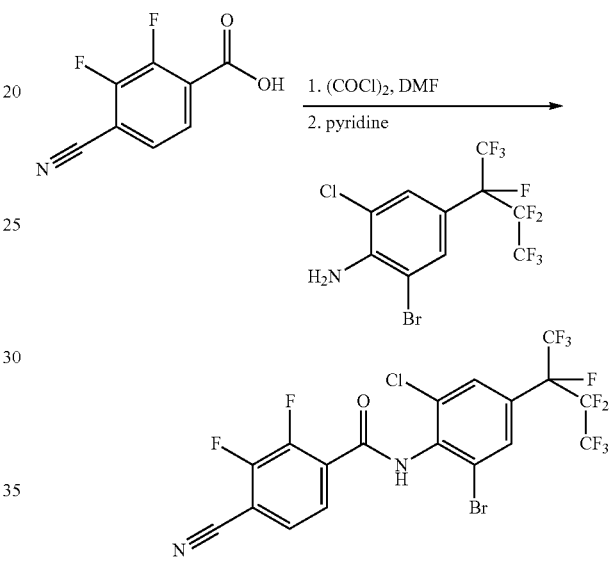

To a solution of 4-cyano-2,3-difluorobenzoic acid (prepared as described in WO 2008/074427) (1.831 g, 10 mmol) and N,N-dimethylformamide ("DMF") (2 drops) in dichloromethane (100 ml) under a nitrogen atmosphere was added oxalyl chloride (1.27 ml, mmol). The reaction mixture was stirred for one hour at ambient temperature and then at 60° C. for 1.5 hours. The reaction mixture was concentrated and the residue dissolved in tetrahydrofuran (75 ml). The solution was added dropwise to a solution of 2-bromo-6-chloro-4-(1,2,2,3,3,3-hexafluoro-1-trifluoromethylpropyl)phenylamine (Example 3.3) (4.245 g, 10 mmol) in a mixture of pyridine (1.6 ml, 20 mmol) and tetrahydrofuran (25 ml). The reaction mixture was stirred at ambient temperature for 16 hours. The reaction mixture was poured into aqueous sodium hydrogen carbonate (1M) and the mixture extracted three times with ethyl acetate. The combined organic phases were dried over sodium sulfate and concentrated. The residue was purified by column chromatography on silica gel (eluent: cyclohexane/ethyl acetate 8:2) to give N-[2-bromo-6-chloro-4-(1,2,2,3,3,3-hexafluoro-1-trifluoromethylpropyl)-henyl]-4-cyano-2,3-difluorobenzamide (4.18 g, 71% yield).

LC-MS (Method 2): RT=2.14, $[M-H]^-=587$.

Similarly, 4-cyano-N-(2,6-dimethyl-4-undecafluorocyclohexylphenyl)-3-nitro-benzamide was made from 2,6-dimethyl-4-undecafluorocyclohexylphenylamine (Example 3.1) and 4-cyano-3-nitrobenzoic acid (prepared as described in WO 2008/074427).

LC-MS (Method 2): RT=2.16, [M–H]⁻=574.

Similarly, 4-cyano-N-[2,6-dimethyl-4-(1,2,2,3,3,3-hexafluoro-1-trifluoromethyl-propyl)phenyl]-3-nitrobenzamide was made from 2,6-dimethyl-4-(1,2,2,3,3,3-hexafluoro-1-trifluoromethylpropyl)phenylamine (Example 3.1) and 4-cyano-3-nitrobenzoic acid (prepared as described in WO 2008/074427). LC-MS (Method 2): RT=2.07, [M–H]⁻= 512.

Similarly, N-[2-chloro-4-(1,2,2,3,3,3-hexafluoro-1-trifluoromethylpropyl)-6-methylthiophenyl]-4-cyano-3-nitrobenzamide was made from 2-chloro-4-(1,2,2,3,3,3-hexafluoro-1-trifluoromethylpropyl)-6-methylthiophenylamine (Example 3.4) and 4-cyano-3-nitrobenzoic acid (prepared as described in WO 2008/074427).

LC-MS (Method 2): RT=2.12, [M–H]⁻=564.

Example 1.5

3-amino-N-[2-bromo-6-chloro-4-(1,2,2,3,3,3-hexafluoro-1-trifluoromethyl-propyl)phenyl]-4-cyanobenzamide

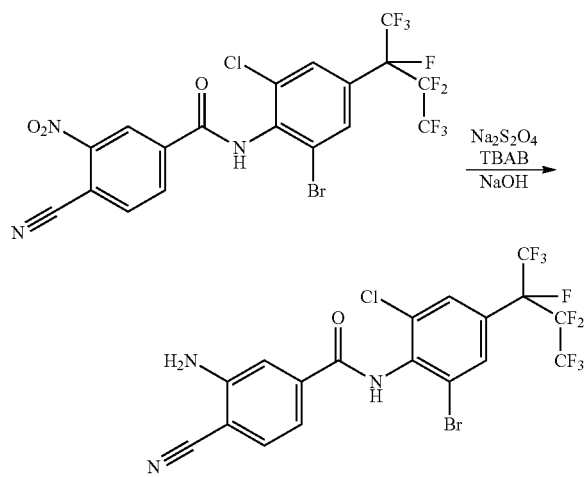

To a solution of N-[2-bromo-6-chloro-4-(1,2,2,3,3,3-hexafluoro-1-trifluoromethyl-propyl)phenyl]-4-cyano-3-nitrobenzamide (Example 1.1) (92.7 g, 154.8 mmol) in tetrahydrofuran (800 ml) was added aqueous sodium hydroxide (0.1 M) (270 ml), sodium hydrosulfite (80.9 g, 464.4 mmol) and tetrabutylammonium bromide ("TBAB") (4.99 g, 15.5 mmol). The reaction mixture was stirred at ambient temperature for 90 minutes. The phases were separated. The aqueous phase was extracted twice with ethyl acetate. The combined organic extracts were washed with water, aqueous sodium hydrogen carbonate (10% w/v) (400 ml) and brine, dried over sodium sulfate and concentrated. The residue was purified by column chromatography on silica gel (eluent:cyclohexane/ethyl acetate 5:1) to give 3-amino-N-[2-bromo-6-chloro-4-(1,2,2,3,3,3-hexafluoro-1-trifluoromethylpropyl)phenyl]-4-cyanobenzamide (69 g, 78.4% yield). ¹H NMR (400 MHz, CDCl₃): 7.82 (s, 1H), 7.75 (s, 1H), 7.71 (s, 1H), 7.51 (m, 1H), 7.35 (s, 1H), 7.21 (m, 1H), 4.7 (s, 2H).

Similarly, 3-amino-4-cyano-N-[2,6-dichloro-3-fluoro-4-(1,2,2,2-tetrafluoro-1-trifluoromethylethyl)phenyl]benzamide was made from 4-cyano-N-[2,6-dichloro-3-fluoro-4-(1,2,2,2-tetrafluoro-1-trifluoromethylethyl)phenyl]-3-nitrobenzamide (Example 1.2).

LC-MS (Method 2): RT=2.00, [M–H]⁻=490.

Similarly, 3-amino-4-cyano-N-[2-ethyl-6-methyl-4-(2,2,3,3,3-pentafluoro-1-hydroxy-1-trifluoromethylpropyl)phenyl]benzamide was made from 4-cyano-N-[2-ethyl-6-methyl-4-(2,2,3,3,3-pentafluoro-1-hydroxy-1-trifluoromethylpropyl)phenyl]-3-nitrobenzamide (Example 1.2). LC-MS (Method 2): RT=1.87, [M+H]⁺=498.

Similarly, 3-amino-4-cyano-N-[2,6-dibromo-4-(1,2,2,3,3,3-hexafluoro-1-trifluoromethylpropyl)phenyl]benzamide was made from 4-cyano-N-[2,6-dibromo-4-(1,2,2,3,3,3-hexafluoro-1-trifluoromethylpropyl)phenyl]-3-nitrobenzamide (Example 1.3).

LC-MS (Method 2): RT=2.06, [M+H]⁺=614.

Similarly, 3-amino-4-cyano-N-[2-methoxy-6-methyl-4-(1,2,2,3,3,3-hexafluoro-1-trifluoromethylpropyl)phenyl]benzamide was made from 4-cyano-N-[2-methoxy-6-methyl-4-(1,2,2,3,3,3-hexafluoro-1-trifluoromethylpropyl)phenyl]-3-nitrobenzamide (Example 1.3).

LC-MS (Method 1): RT=1.99, [M–H]⁻=498.

Similarly, 3-amino-4-cyano-N-[2,6-dichloro-4-(1,2,2,3,3,3-hexafluoro-1-trifluoromethylpropyl)phenyl]benzamide was made from 4-cyano-N-[2,6-dichloro-4-(1,2,2,3,3,3-hexafluoro-1-trifluoromethylpropyl)phenyl]-3-nitrobenzamide (Example 1.3).

LC-MS (Method 2): RT=2.01, [M+H]⁺=524/526.

Similarly, 3-amino-4-cyano-N-(2,6-dimethyl-4-undecafluorocyclohexylphenyl)-benzamide was made from 4-cyano-N-(2,6-dimethyl-4-undecafluorocyclohexylphenyl)-3-nitrobenzamide (Example 1.4). LC-MS (Method 2): RT=2.10, [M+H]⁺=546.

Similarly, 3-amino-4-cyano-N-[4-(1,2,2,3,3,3-hexafluoro-1-trifluoromethylpropyl)-2,6-dimethylphenyl]benzamide was made from 4-cyano-N-[2,6-dimethyl-4-(1,2,2,3,3,3-hexafluoro-1-trifluoromethylpropyl)phenyl]-3-nitrobenzamide (Example 1.4).

LC-MS (Method 2): RT=2.00, [M–H]⁻=482.

Similarly, benzoic acid 1-[4-(3-amino-4-cyanobenzoylamino)-3-bromo-5-chloro-phenyl]-2,2,2-trifluoro-1-trifluoromethylethyl ester was made from benzoic acid 1-[3-bromo-5-chloro-4-(4-cyano-3-nitrobenzoylamino)phenyl]-2,2,2-trifluoro-1-trifluoromethylethyl ester (Example 1.2). ¹H NMR (CDCl₃, 400 MHz): 8.12 (d, 2H), 7.72 (m, 1H), 7.68 (s, 1H), 7.51-7.59 (m, 4H), 7.32 (s, 1H), 7.20 (d, 1H), 4.64 (bs, 2H).

Similarly, 3-amino-4-cyano-N-[2,6-dichloro-4-(1,2,2,2-tetrafluoro-1-trifluoromethyl-ethyl)phenyl]benzamide was made from 4-cyano-N-[2,6-dichloro-4-(1,2,2,2-tetrafluoro-1-trifluoromethylethyl)phenyl]-3-nitrobenzamide (Example 1.3).

LC-MS (Method 3, positive): RT=1.98, [M–H]⁻=474 (M+H⁺).

Similarly, 3-amino-N-[2-bromo-6-chloro-4-(1,2,2,2-tetrafluoro-1-trifluoromethyl-ethyl)phenyl]-4-cyanobenzamide was made from N-[2-bromo-6-chloro-4-(1,2,2,2-tetrafluoro-1-trifluoromethylethyl)phenyl]-4-cyano-3-nitrobenzamide (Example 1.2). ¹H NMR (CDCl₃, 400 MHz): 7.83 (s, 1H), 7.71 (s, 1H), 7.54 (m, 2H), 7.32 (s, 1H), 7.22 (d, 1H), 4.64 (bs, 2H).

Example 1.6

3-amino-N-[2-chloro-4-(1,2,2,3,3,3-hexafluoro-1-trifluoromethylpropyl)-6-methylthiophenyl]-4-cyanobenzamide

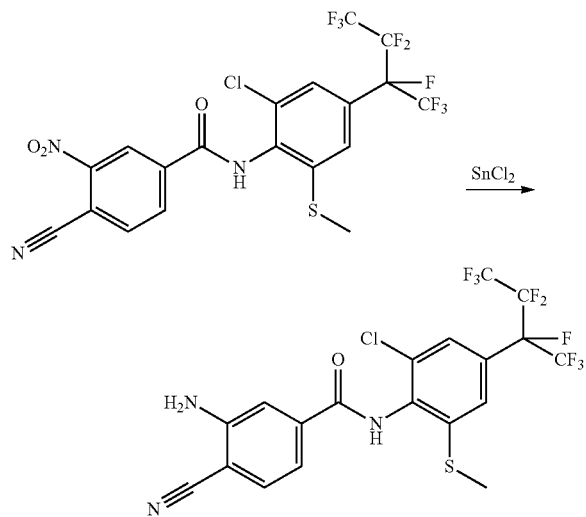

To a solution of N-[2-chloro-4-(1,2,2,3,3,3-hexafluoro-1-trifluoromethylpropyl)-6-methylthiophenyl]-4-cyano-3-nitrobenzamide (Example 1.4) (13.0 g, 23 mmol) in isopropanol (110 ml) was added tin chloride (15.69 g, 82.8 mmol). The mixture was cooled to 0° C. and aqueous hydrochloric acid (37% w/v) (22 ml) was added slowly. The mixture was stirred at 80° C. for 1 hours. About one third of the total volume of isopropanol was evaporated. Water (100 ml) was added to the mixture followed by aqueous sodium hydroxide (4N) to adjust the pH to 8 to 9. The aqueous phase was extracted three times with ethyl acetate (20 ml). The combined organic extracts were dried over sodium sulfate and concentrated. The residue was purified by column chromatography on silica gel (eluent: ethyl acetate/cyclohexane 1:2 to 1:1) to give 3-amino-N-[2-chloro-4-(1,2,2,3,3,3-hexafluoro-1-trifluoromethylpropyl)-6-methylthiophenyl]-4-cyanobenzamide (5.65 g, 45.8% yield). LC-MS (Method 1): RT=2.03, [M−H]$^-$=536.

Example 1.7

3-amino-N-[2-bromo-6-chloro-4-(1,2,2,3,3,3-hexafluoro-1-trifluoromethyl-propyl)phenyl]-4-cyano-2-fluorobenzamide

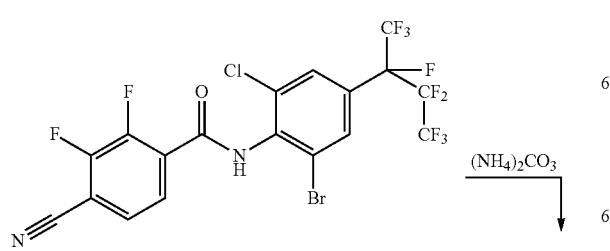

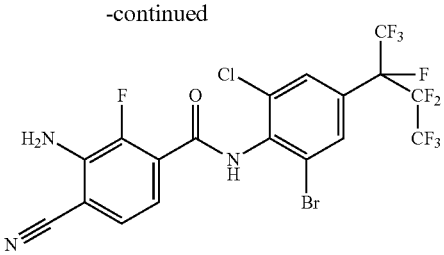

To a solution of N-[2-bromo-6-chloro-4-(1,2,2,3,3,3-hexafluoro-1-trifluoromethyl-propyl)phenyl]-4-cyano-2,3-difluorobenzamide (Example 1.4) (4.08 g, 6.92 mmol) in dimethylsulfoxide (69 ml) was added ammonium carbonate (1.529 g, 15.92 mmol). The reaction mixture was heated to 100° C. for 16 hours. The reaction mixture was allowed to cool to ambient temperature and then partitioned between water and ethyl acetate. The organic phase was dried over sodium sulfate and concentrated. The residue was purified by column chromatography on silica gel (eluent:cyclohexane/ethyl acetate 8:2) to give 3-amino-N-[2-bromo-6-chloro-4-(1,2,2,3,3,3-hexafluoro-1-trifluoromethylpropyl)phenyl]-4-cyano-2-fluorobenzamide (1.88 mg, 46.3% yield).

LC-MS (Method 2): RT=2.06, [M−H]$^-$=584.

Similarly, 3-amino-4-cyano-N-[2,6-dichloro-4-(1,2,2,3,3,3-hexafluoro-1-trifluoromethylpropyl)phenyl]-2-fluorobenzamide was made from 4-cyano-N-[2,6-dichloro-4-(1,2,2,3,3,3-hexafluoro-1-trifluoromethylpropyl)phenyl]-2,3-difluorobenzamide (Example 1.2). LC-MS (Method 2): RT=2.03, [M−H]$^-$=540.

2. Preparation of Compounds of Formula (I)

Example 2.1

4-cyano-3-(4'-cyano-2'-methylbenzoylamino)-N-[2,6-dibromo-4-(1,2,2,3,3,3-hexafluoro-1-trifluoromethylpropyl)phenyl]benzamide (Compound No. A4 of Table A)

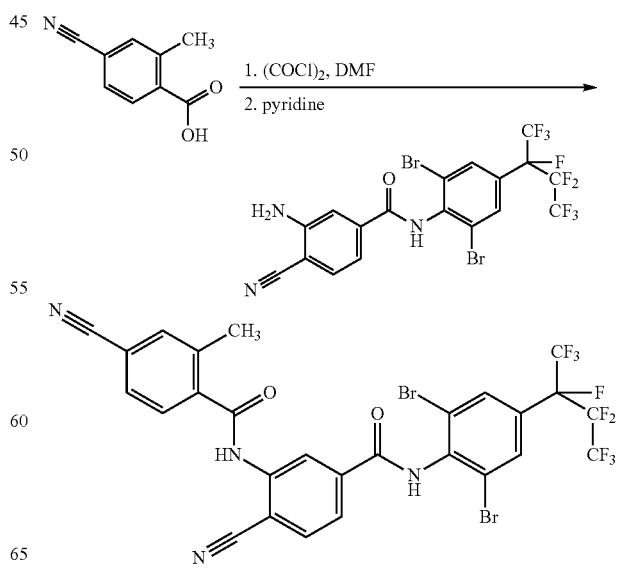

To a suspension of 4-cyano-2-methylbenzoic acid (Example 3.7) (0.5 g, 3.10 mmol) in dichloromethane (5 ml) was added oxalyl chloride (0.315 ml, 3.72 mmol) at ambient temperature, followed by N,N-dimethylformamide ("DMF") (2 drops). The reaction mixture was stirred for 30 minutes at ambient temperature and then heated to reflux for 30 minutes. The reaction mixture was allowed to cool to ambient temperature, concentrated and the residue suspended in tetrahydrofuran (5 ml). A solution of 3-amino-4-cyano-N-[2,6-dibromo-4-(1,2,2,3,3,3-hexafluoro-1-trifluoromethylpropyl)phenyl]benzamide (Example 1.5) (1.43 g, 2.30 mmol) in a mixture of tetrahydrofuran (5 ml) and pyridine (0.498 ml, 6.2 mmol) was cooled to 0° C. and the solution of 4-cyano-2-methylbenzoyl chloride was added. The reaction mixture was stirred at ambient temperature for 30 minutes, then the mixture reaction was stirred at 80° C. for 16 hours. Saturated aqueous sodium hydrogen carbonate (30 ml) was added and the mixture extracted twice with ethyl acetate (2×20 ml). The combined organic extracts were dried over sodium sulfate and concentrated. The residue was purified by column chromatography on silica gel (eluent:cyclohexane/ethyl acetate 4:1) to give Compound No. A4 of Table A (0.752 g, 43% yield).

Similarly, 4-cyano-3-(4'-cyano-2'-methylbenzoylamino)-N-[2-ethyl-6-methyl-4-(1,2,2,3,3,3-hexafluoro-1-trifluoromethylpropyl)phenyl]benzamide (Compound No. A1 of Table A) was made from 3-amino-4-cyano-N-[2-ethyl-6-methyl-4-(1,2,2,3,3,3-hexafluoro-1-trifluoromethylpropyl)phenyl]benzamide (made as in WO 2008/074427).

Similarly, N-[2-bromo-6-chloro-4-(1,2,2,3,3,3-hexafluoro-1-trifluoromethylpropyl)-phenyl]-4-cyano-3-(4'-cyano-2'-methylbenzoylamino)benzamide (Compound No. A2 of Table A) was made from 3-amino-N-[2-bromo-6-chloro-4-(1,2,2,3,3,3-hexafluoro-1-trifluoromethylpropyl)phenyl]-4-cyanobenzamide (Example 1.5).

Similarly, 4-cyano-3-(4'-cyano-2'-methylbenzoylamino)-N-[2,6-dibromo-4-(1,2,2,2-tetrafluoro-1-trifluoromethylethyl)phenyl]benzamide (Compound No. A3 of Table A) was made from 3-amino-4-cyano-N-[2,6-dibromo-4-(1,2,2,3,3,3-tetrafluoro-1-trifluoromethyl-ethyl)phenyl]benzamide (prepared as described in WO 2008/074427).

Similarly, N-[2-bromo-6-ethyl-4-(1,2,2,3,3,3-hexafluoro-1-trifluoromethylpropyl)-phenyl]-4-cyano-3-(4'-cyano-2'-methylbenzoylamino)benzamide (Compound No. A5 of Table A) was made from 3-amino-N-[2-bromo-6-ethyl-4-(1,2,2,3,3,3-hexafluoro-1-trifluoromethylpropyl)phenyl]-4-cyanobenzamide (prepared as described in WO 2008/074427).

Similarly, N-[2-bromo-6-chloro-4-(1,2,2,3,3,3-hexafluoro-1-trifluoromethylpropyl)-phenyl]-4-cyano-3-(4'-cyano-2'-methylbenzoylamino)-2-fluorobenzamide (Compound No. A6 of Table A) was made from 3-amino-N-[2-bromo-6-chloro-4-(1,2,2,3,3,3-hexafluoro-1-trifluoromethylpropyl)phenyl]-4-cyano-2-fluorobenzamide (Example 1.7).

Similarly, 4-cyano-3-(4'-cyano-2'-methylbenzoylamino)-N-[2,6-dichloro-4-(1,2,2,3,3,3-hexafluoro-1-trifluoromethylpropyl)phenyl]benzamide (Compound No. A8 of Table A) was made from 3-amino-4-cyano-N-[2,6-dichloro-4-(1,2,2,3,3,3-hexafluoro-1-trifluoromethylpropyl)phenyl]benzamide (Example 1.5).

Similarly, 4-cyano-3-(4'-cyano-2'-methyl-benzoylamino)-N-[4-(1,2,2,3,3,3-hexafluoro-1-trifluoromethylpropyl)-2-methoxymethyl-6-methylphenyl]benzamide (Compound No. A9 of Table A) was made from 3-amino-4-cyano-N-[4-(1,2,2,3,3,3-hexafluoro-1-trifluoromethylpropyl)-2-methoxymethyl-6-methylphenyl]benzamide (prepared as described in WO 2008/074427).

Similarly, N-[2-chloro-4-(1,2,2,3,3,3-hexafluoro-1-trifluoromethylpropyl)-6-methylthiophenyl]-4-cyano-3-(4'-cyano-2'-methylbenzoylamino)benzamide (Compound No. A10 of Table A) was made from 3-amino-N-[2-chloro-4-(1,2,2,3,3,3-hexafluoro-1-trifluoromethylpropyl)-6-methylthiophenyl]-4-cyanobenzamide (Example 1.6).

Similarly, 4-cyano-3-(4'-cyano-2'-methylbenzoylamino)-N-[2-methoxy-6-methyl-4-(1,2,2,3,3,3-hexafluoro-1-trifluoromethylpropyl)phenyl]benzamide (Compound No. A11 of Table A) was made from 3-amino-4-cyano-N-[2-methoxy-6-methyl-4-(1,2,2,3,3,3-hexafluoro-1-trifluoromethylpropyl)phenyl]benzamide (Example 1.5).

Similarly, benzoic acid 1-{3-bromo-5-chloro-4-[4-cyano-3-(4-cyano-2-methyl-benzoylamino)benzoylamino]phenyl}-2,2,2-trifluoro-1-trifluoromethylethyl ester (Compound No. A12 of Table A) was made from benzoic acid 1-[4-(3-amino-4-cyano-benzoylamino)-3-bromo-5-chlorophenyl]-2,2,2-trifluoro-1-trifluoromethylethyl ester (Example 1.5). $^1$H NMR (CDCl$_3$, 400 MHz): 9.08 (s, 1H), 8.11 (m, 3H), 7.78 (s, 1H), 7.88 (m, 1H), 7.82 (m, 1H), 7.52-7.75 (m, 8H), 2.60 (s, 3H).

Similarly, 4-cyano-3-(4'-cyano-2'-methylbenzoylamino)-N-[2,6-dichloro-3-fluoro-4-(1,2,2,2-tetrafluoro-1-trifluoromethylethyl)phenyl]benzamide (Compound No. A 14 of Table A) was made from 3-amino-4-cyano-N-[2,6-dichloro-3-fluoro-4-(1,2,2,2-tetrafluoro-1-trifluoromethylethyl)phenyl]benzamide (Example 1.5).

Similarly, 4-cyano-3-(4'-cyano-2'-methyl-benzoylamino)-N-[2-ethyl-6-methyl-4-(2,2,3,3,3-pentafluoro-1-hydroxy-1-trifluoromethylpropyl)phenyl]benzamide (Compound No. A15 of Table A) was made from 3-amino-4-cyano-N-[2-ethyl-6-methyl-4-(2,2,3,3,3-pentafluoro-1-hydroxy-1-trifluoromethylpropyl)phenyl]benzamide (Example 1.5).

Similarly, 4-cyano-3-(4'-cyano-2'-methyl-benzoylamino)-N-[2,6-dimethyl-4-(1,2,2,3,3,3-hexafluoro-1-trifluoromethylpropyl)phenyl]benzamide (Compound No. A16 of Table A) was made from 3-amino-4-cyano-N-[2,6-dimethyl-4-(1,2,2,3,3,3-hexafluoro-1-trifluoromethylpropyl)phenyl]benzamide (Example 1.5).

Similarly, 4-cyano-3-(4'-cyano-2'-methylbenzoylamino)-N-[2,6-dimethyl-4-(undecafluorocyclohexyl)phenyl]benzamide (Compound No. A17 of Table A) was made from 3-amino-4-cyano-N-[2,6-dimethyl-4-(undecafluorocyclohexyl)phenyl]benzamide (Example 1.5).

Similarly, 4-cyano-3-(4'-cyano-2'-methylbenzoylamino)-N-[2,6-dichloro-4-(1,2,2,2-tetrafluoro-1-trifluoromethylethyl)phenyl]benzamide (Compound No. A19 of Table A) was made from 3-amino-4-cyano-N-[2,6-dichloro-4-(1,2,2,2-tetrafluoro-1-trifluoromethylethyl)-phenyl]benzamide (Example 1.5).

Similarly, 4-cyano-3-(4'-cyano-2'-methylbenzoylamino)-N-[2-bromo-6-chloro-4-(1,2,2,2-tetrafluoro-1-trifluoromethylethyl)phenyl]benzamide (Compound No. A20 of Table A) was made from 3-amino-N-[2-bromo-6-chloro-4-(1,2,2,2-tetrafluoro-1-trifluoromethyl-ethyl)phenyl]-4-cyanobenzamide (Example 1.5).

$^1$H NMR (CDCl$_3$, 400 MHz): 9.08 (s, 1H), 8.24 (sb, 1H), 8.15 (sb, 1H), 7.92-7.82 (m, 3H), 7.74 (s, 1H), 7.68 (m, 1H), 7.62 (m, 2H), 2.59 (s, 3H).

Example 2.2

4-cyano-3-(4'-cyano-2'-methylbenzoylamino)-N-[2,6-dichloro-4-(1,2,2,3,3,3-hexafluoro-1-trifluoromethylpropyl)phenyl]-2-fluorobenzamide (Compound No. A18 of Table A)

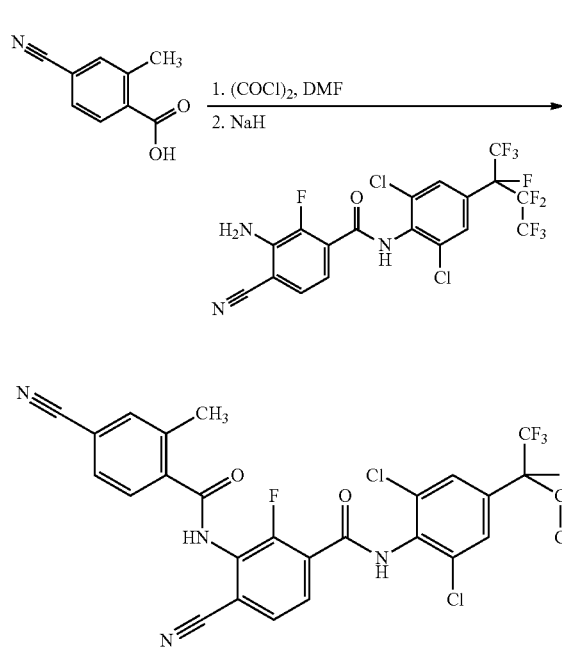

To a suspension of 3-amino-4-cyano-N-[2,6-dichloro-4-(1,2,2,3,3,3-hexafluoro-1-trifluoromethylpropyl)phenyl]-2-fluorobenzamide (Example 1.7) (0.054 g, 0.10 mmol) in N,N-dimethylacetamide ("DMA") (1 ml) was added sodium hydride (55% w/v) (0.018 g, 0.40 mmol). The reaction mixture was stirred for 30 minutes at ambient temperature and then 4-cyano-2-methylbenzoyl chloride (see first part of Example 2.1) (0.10 mmol) was added. The reaction mixture was stirred at ambient temperature for 16 hours. Satruated aqueous sodium hydrogen carbonate (30 ml) was added and the organic phase extracted twice with ethyl acetate (2×20 ml). The combined organic extracts were dried over sodium sulfate and concentrated. The residue was purified by column chromatography on silica gel (eluent:cyclohexane/ethyl acetate 7:3) to give Compound No. A18 of Table A (0.010 g, 15% yield).

Example 2.3

N-[2-chloro-6-cyano-4-(1,2,2,3,3,3-hexafluoro-1-trifluoromethylpropyl)-phenyl]-4-cyano-3-(4'-cyano-2'-methylbenzoylamino)benzamide (Compound No. A7 of Table A)

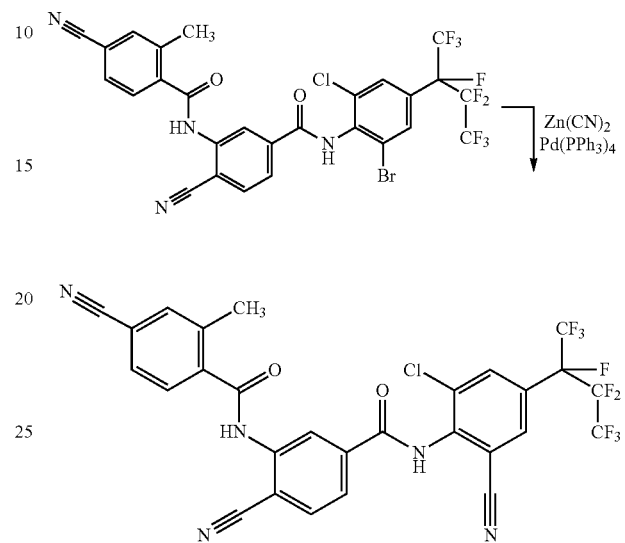

To a solution of Compound No. A2 of Table A (Example 2.1) (1 g, 1.4 mmol) in N,N-dimethylformamide (12 ml) under a nitrogen atmosphere was added zinc (II) cyanide (0.26 g, 2.25 mmol) and tetrakis(triphenylphosphine)palladium(0) (0.195 g, 0.17 mmol).

The reaction mixture was stirred at 130° C. for 2 hours. The reaction mixture was diluted with toluene and the phases were separated. The aqueous phase was extracted twice with toluene. The combined organic phases were washed with brine and saturated aqueous ammonium hydroxide, dried over sodium sulfate and concentrated. The residue was purified by column chromatography on silica gel (eluent: ethyl acetate/cyclohexane 1:5) to give Compound No. A7 of Table A (0.421 g, 45.5% yield).

Example 2.4

N-[2-bromo-6-chloro-4-[1,1,1,3,3,3-hexafluoropropan-2-ol)phenyl]-4-cyano-3-(4'-cyano-2'-methylbenzoylamino)benzamide (Compound No. A13 of Table A)

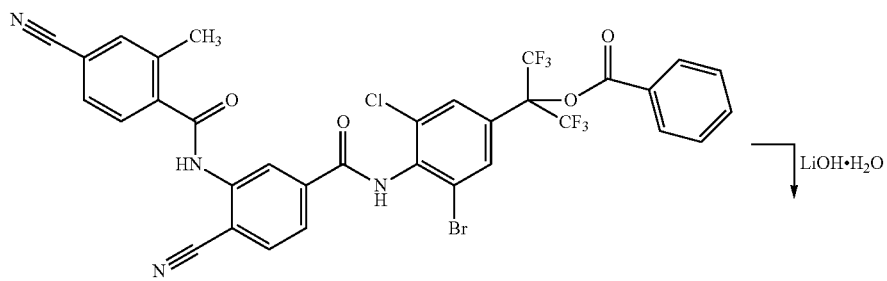

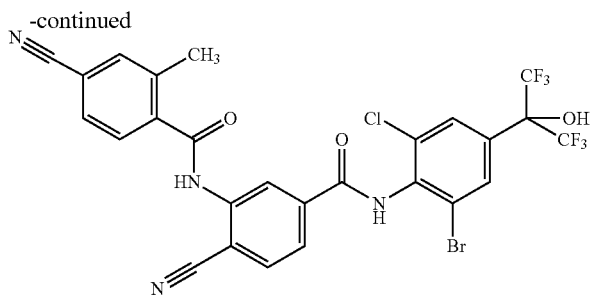

To a solution of Compound No. A12 of Table A (Example 2.1) (0.252 g, 0.33 mmol) in a mixture of tetrahydrofuran (10 ml) and water (2.5 ml) was added lithium hydroxide (0.030 g). The reaction mixture was stirred at ambient temperature for 16 hours. The reaction mixture was diluted with water and ethyl acetate and the phases were separated. The aqueous phase was extracted twice with ethyl acetate. The combined organic phases were dried over sodium sulfate and concentrated. The residue was purified by column chromatography on silica gel (eluent: ethyl acetate/cyclohexane 1:3) to give Compound No. A13 of Table A (0.09 g, 41% yield). $^1$H NMR (CDCl$_3$, 400 MHz): 9.09 (s, 1H), 8.08 (s, 1H), 7.95 (s, 1H), 7.82-7.93 (m, 4H), 7.62-7.70 (m, 3H), 4.02 (bs, OH), 2.62 (s, 3H).

3. Preparation of Building Blocks

Example 3.1

4-(1,2,2,3,3,3-hexafluoro-1-trifluoromethylpropyl)-2-methoxy-6-methyl-phenylamine

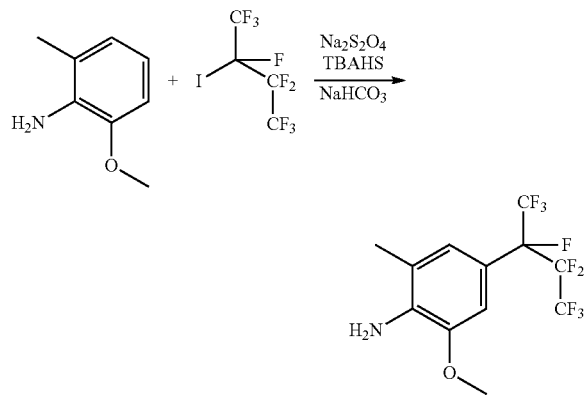

To a solution of 2-methoxy-6-methylphenylamine (8.23 g, 60 mmol) in a mixture of water (60 ml) and tert-butyl methyl ether (60 ml) was added, successively 2-iodononafluorobutane (24.9 g, 11.86 ml, 72 mmol), sodium hydrosulfite (15.29 g, 72 mmol), sodium hydrogen carbonate (6.05 g, 72.0 mmol) and tetrabutyl ammonium hydrogen sulfate ("TBAHS") (2.24 g, 6.60 mmol). The reaction mixture was stirred at ambient temperature for 16 hours. The mixture was filtered and the filtrate was extracted twice with tert-butyl methyl ether. The combined organic phases were washed with aqueous hydrochloric acid (1N), dried over sodium sulfate and concentrated to give 4-(1,2,2,3,3,3-hexafluoro-1-trifluoromethylpropyl)-2-methoxy-6-methylphenylamine which was used without further purification. LC-MS (Method 2): RT=2.05, [M+H]$^+$=356.

Similarly, 3-fluoro-4-(1,2,2,2-tetrafluoro-1-trifluoromethylethyl)phenylamine was made from 3-fluorophenylamine and 2-iodohexafluoropropane.
LC-MS (Method 2): RT=1.86, [M+H]$^+$=280.

Similarly, 4-(1,2,2,3,3,3-hexafluoro-1-trifluoromethylpropyl)-2-methylthio-phenylamine was made from 2-methylthiophenylamine and 2-iodononafluorobutane. $^1$H NMR (400 MHz, CDCl$_3$): 7.59 (s, 1H), 7.29 (m, 1H), 6.79 (d, 1H).

Similarly, 2,6-dimethyl-4-undecafluorocyclohexylphenylamine was made from 2,6-dimethylphenylamine and iodoperfluorocyclohexane.
LC-MS (Method 2): RT=2.18, [M+H]$^+$=402.

Similarly, 2,6-dimethyl-4-(1,2,2,3,3,3-hexafluoro-1-trifluoromethylpropyl)-phenylamine was made from 2,6-dimethylphenylamine and 2-iodononafluorobutane. LC-MS (Method 2): RT=2.06, [M+H]$^+$=340.

Example 3.2

2,6-dibromo-4-(1,2,2,3,3,3-hexafluoro-1-trifluoromethylpropyl)phenylamine

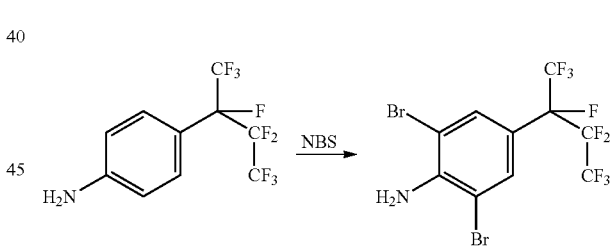

To a solution of 4-(1,2,2,3,3,3-hexafluoro-1-trifluoromethylpropyl)phenylamine (prepared as described in EP 1,006, 102) (56 g, 180 mmol) in dichloromethane (500 ml) was added N-bromo-succinimide ("NBS") (76.9 g, 432 mmol). The reaction mixture was stirred at ambient temperature for 2 hours. The reaction mixture was concentrated and the residue partitioned between ethyl acetate (200 ml) and water (200 ml). The phases were separated and the aqueous phase was extracted twice with ethyl acetate. The combined organic extracts were dried over sodium sulfate and concentrated. The residue was purified by column chromatography on silica gel (eluent:cyclohexane/ethyl acetate 8:2) to give 2,6-dibromo-4-(1,2,2,3,3,3-hexafluoro-1-trifluoromethylpropyl)phenylamine (51.6 g, 61.1% yield). $^1$H NMR (400 MHz, CDCl$_3$): 7.58 (s, 2H), 4.90 (bs, 2H).

Similarly, 2,6-dichloro-4-(1,2,2,3,3,3-hexafluoro-1-trifluoromethylpropyl)-phenylamine was made from 4-(1,2,2,3,3-hexafluoro-1-trifluoromethylpropyl)-phenylamine (prepared as described in EP 1,006,102) and N-chlorosuccinimide ("NCS"). ¹H NMR (400 MHz, CDCl₃): 7.39 (s, 2H), 4.76 (bs, 2H).

Similarly, 2,6-dichloro-3-fluoro-4-(1,2,2,2-tetrafluoro-1-trifluoromethylethyl)-phenylamine was made from 3-fluoro-4-(1,2,2,2-tetrafluoro-1-trifluoromethylethyl)-phenylamine (Example 3.1) and N-chlorosuccinimide ("NCS").

¹H NMR (400 MHz, CDCl₃): 7.40 (d, 1H), 4.92 (bs, 2H).

Example 3.3

2-bromo-6-chloro-4-(1,2,2,3,3,3-hexafluoro-1-trifluoromethylpropyl)-phenylamine

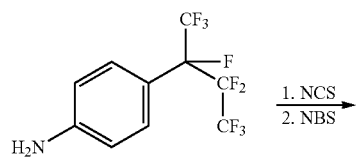

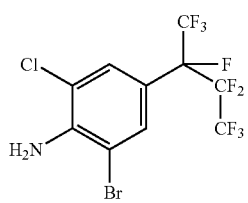

4-(1,2,2,3,3,3-Hexafluoro-1-trifluoromethylpropyl)phenylamine (prepared as described in EP 1,006,102) (175.8 g, 565 mmol) was dissolved in acetonitrile (1000 ml) and N-chloro-succinimide ("NCS") (76.2 g, 570.7 mmol) was added. The reaction mixture was heated to reflux for 90 minutes. The reaction mixture was concentrated, the residue suspended in diethyl ether and the solids removed via filtration. The filtrate was concentrated and the residue was purified by column chromatography on silica gel (eluent: cyclohexane/dichloromethane 9:1) to give 2-chloro-4-(1,2,2,3,3,3-hexafluoro-1-trifluoromethylpropyl)phenylamine. The same procedure was repeated using N-bromosuccinimide ("NBS") (100.5 g, 565 mmol) as reagent. This time the residue was purified by column chromatography on silica gel (eluent: cyclohexane/dichloromethane 2:1) to give 2-bromo-6-chloro-4-(1,2,2,3,3,3-hexafluoro-1-trifluoromethylpropyl) phenylamine (143.3 g, 59.7% yield). ¹H NMR (400 MHz, CDCl₃): 7.70 (s, 1H), 7.42 (s, 1H), 4.82 (s, 2H).

Similarly, 2-(4-amino-3-bromo-5-chlorophenyl)-1,1,1,3,3,3-hexafluoropropan-2-ol was made from [4-[2,2,2-trifluoro-1-hydroxy-1-(trifluoromethyl)ethyl]phenyl]amine. ¹H NMR (400 MHz, CDCl₃): 7.68 (s, 1H), 7.46 (s, 1H), 4.72 (bs, 2H).

Similarly, 2-bromo-6-chloro-4-(1,2,2,2-tetrafluoro-1-trifluoromethylethyl)-phenylamine was made from 4-(1,2,2,2-tetrafluoro-1-trifluoromethylethyl)phenylamine (prepared as described in EP 1,006,102).

¹H NMR (400 MHz, CDCl₃): 7.58 (s, 1H), 7.45 (s, 1H), 4.82 (bs, 2H).

Example 3.4

2-chloro-4-(1,2,2,3,3,3-hexafluoro-1-trifluoromethylpropyl)-6-methylthio-phenylamine

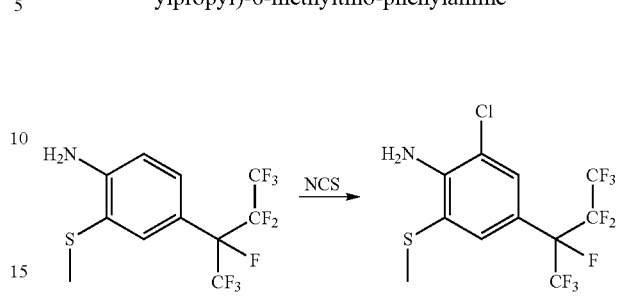

To a solution of 4-(1,2,2,3,3,3-hexafluoro-1-trifluoromethylpropyl)-2-methylthio-phenylamine (Example 3.1) (21.85 g, 61.16 mmol) in acetonitrile (170 ml) was added N-chlorosuccinimide ("NCS") (8.578 g, 64.22 mmol). The reaction mixture was stirred at ambient temperature for 16 hours. The reaction mixture was concentrated and the residue partitioned between ethyl acetate (100 ml) and water (100 ml). The phases were separated and the aqueous phase was extracted twice with ethyl acetate. The combined organic extracts were dried over sodium sulfate and concentrated. The residue was purified by column chromatography on silica gel (eluent:cyclohexane/ethyl acetate 4:1) to give 2-chloro-4-(1,2,2,3,3,3-hexafluoro-1-trifluoromethylpropyl)-6-methylthiophenylamine (12.0 g, 50% yield). LC-MS (Method 2): RT=2.17, [M–H]⁻=392.

Example 3.5

2-(4-amino-3-ethyl-5-methylphenyl)-1,1,1,3,3,4,4,4-octafluorobutan-2-ol

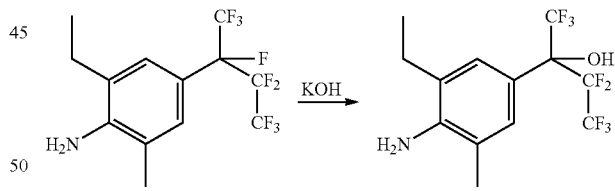

To a solution of 2-ethyl-4-(1,2,2,3,3,3-hexafluoro-1-trifluoromethylpropyl)-6-methyl-phenylamine (prepared as descriebed in WO 2008/074427) (3.88 g, 11 mmol) in a mixture of acetonitrile (320 ml) and water (80 ml) was added potassium hydroxide (46.2 g, 827 mmol). The reaction mixture was stirred at 70° C. for 2 days. The reaction mixture was diluted with water (200 ml) and the mixture extracted three times with ethyl acetate (200 ml). The combined organic extracts were dried over sodium sulfate and concentrated. The residue was purified by column chromatography on silica gel (eluent: ethyl acetate/cyclohexane 1:3) to give 2-(4-amino-3-ethyl-5-methylphenyl)-1,1,1,3,3,4,4,4-octafluorobutan-2-ol (2.31 g, 60% yield). LC-MS (Method 1): RT=1.87, [M–H]⁻=352.

Example 3.6

Preparation of 4-cyano-2-methylbenzoic Acid Methyl Ester

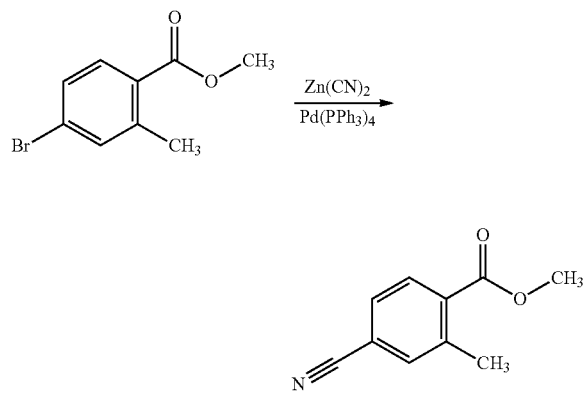

To a solution of 4-bromo-2-methylbenzoic acid methyl ester (108 g, 471 mmol) in N,N-dimethylformamide (4 l) under a nitrogen atmosphere was added zinc (II) cyanide (88.5 g, 753.6 mmol) and tetrakis(triphenylphosphine)palladium(0) (65 g, 56.60 mmol). The reaction mixture was stirred at 100° C. for 16 hours. The reaction mixture was diluted with toluene and the phases were separated. The aqueous phase was extracted twice with toluene. The combined organic phases were washed with brine and saturated aqueous ammonium hydroxide, dried over sodium sulfate and concentrated. The residue was purified by column chromatography on silica gel (eluent: ethyl acetate/cyclohexane 1:5) t give 4-cyano-2-methylbenzoic acid methyl ester (73 g, 89% yield). $^1$H NMR (400 MHz, CDCl$_3$): 7.78 (d, 1H), 7.52 (m, 2H), 3.92 (s, 3H), 2.62 (s, 3H).

Example 3.7

4-cyano-2-methyl-benzoic Acid

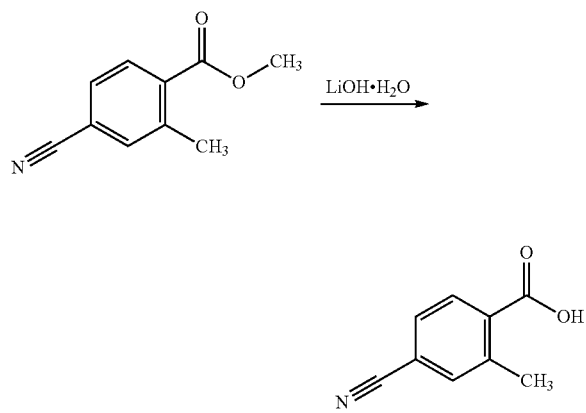

To a solution of 4-cyano-2-methylbenzoic acid methyl ester (Example 3.6) (61 g, 348 mmol) in a mixture of water (0.360 ml) and tetrahydrofuran (1.4 l) was added lithium hydroxide hydrate (31.4 g, 748.2 mmol). The reaction mixture was stirred at ambient temperature for 3 hours. The reaction mixture was concentrated. The residue was acidified by addition of aqueous hydrochloric acid (1N) and extracted with a mixture of methanol and chloroform (5:95). The organic phase was dried over sodium sulfate and concentrated. The residue was crystallized in a mixture of ethyl acetate andcyclohexane to give 4-cyano-2-methylbenzoic acid (55.5 g, 99% yield).
$^1$H NMR (400 MHz, CDCl$_3$): 7.89 (d, 1H), 7.80 (s, 1H), 7.72 (d, 1H), 2.51 (s, 3H).

Example 3.8

Benzoic Acid 1-(4-amino-3-bromo-5-chlorophenyl)-2,2,2-trifluoro-1-trifluoromethylethyl Ester

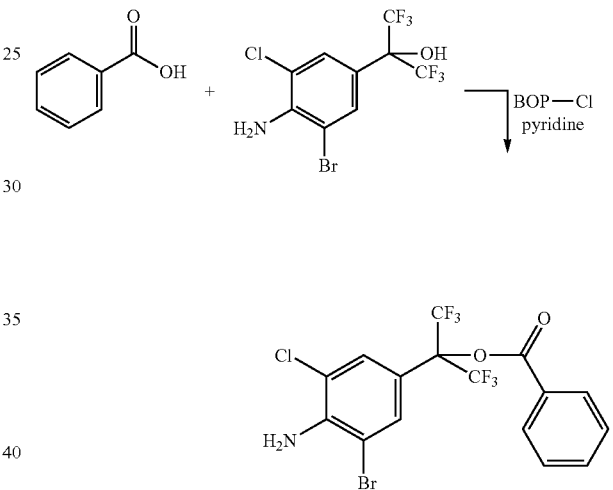

To a solution of 2-(4-amino-3-bromo-5-chlorophenyl)-1,1,1,3,3,3-hexafluoropropan-2-ol (Example 3.3) (3.725 g, 10.0 mmol) and benzoic acid (1.28 g, 10.5 mmol) in dichloromethane (30 ml) was added pyridine (4.18 ml, 30 mmol) and bis(2-oxo-3-oxazolidinyl)phosphonic chloride ("BOP-Cl") (2.80 g, 11 mmol). The reaction mixture was heated to reflux for 24 hours. The reaction mixture was cooled to ambient temperature and quenched by addition of aqueous hydrochloric acid (1N) (50 ml). The mixture was then extracted three times with dichloromethane. The combined organic extracts were washed with saturated aqueous sodium hydrogen carbonate, dried over sodium sulfate and concentrated. The residue was purified by column chromatography on silica gel (Buchi fraction collector C-660, prepacked cartridges Silicagel 60, particle size: 40-63 µm, D 40×150 mm, Gradient 99 to 1% methanol in toluene over 15 min, 60 mL/min, fraction 20 mL) to give benzoic acid 1-(4-amino-3-bromo-5-chlorophenyl)-2,2,2-trifluoro-1-trifluoromethylethyl ester (2 g, 42% yield). $^1$H NMR (400 MHz, CDCl$_3$): 8.18 (d, 1H), 8.11 (d, 1H), 7.68 (m, 1H), 7.53 (m, 2H), 7.41 (s, 1H), 7.29 (s, 1H), 4.74 (bs, 2H).

TABLE A

Structure (I): A phenyl ring bearing CN, NH-C(=O)-(2-methyl-4-cyanophenyl) at position 1, and C(=O)-NH-Q² at position 3, with (R³)ₙ substituents at positions 5/6.

| Comp. No. | R³ | n | Q²/ ¹H NMR (CDCl₃, 400 MHz) | RT (min) | [M + H]⁺ or [M − H]⁻ | LC-MS Method No. |
|---|---|---|---|---|---|---|
| A1 | — | 0 | 2-ethyl-6-methyl-4-(nonafluorobut-2-yl)phenyl | 2.14 | 641(+) | 2 |
| A2 | — | 0 | 2-bromo-6-chloro-4-(nonafluorobut-2-yl)phenyl | 2.13 | 711(−) | 2 |
| A3 | — | 0 | 2,6-dibromo-4-(heptafluoroprop-2-yl)phenyl | 2.08 | 705(−) | 2 |
| A4 | — | 0 | 2,6-dibromo-4-(nonafluorobut-2-yl)phenyl | 2.14 | 755(−) | 2 |
| A5 | — | 0 | 2-bromo-6-ethyl-4-(nonafluorobut-2-yl)phenyl | 2.16 | 707(+) | 2 |
| A6 | 2-F | 1 | 2-bromo-6-chloro-4-(nonafluorobut-2-yl)-phenyl- | 2.11 | 729(−) | 2 |
| A7 | — | 0 | 2-chloro-6-cyano-4-(nonafluorobut-2-yl)phenyl | 2.03 | 656(−) | 2 |
| A8 | — | 0 | 2,6-dichloro-4-(nonafluorobut-2-yl)phenyl | 2.11 | 665(−) | 2 |
| A9 | — | 0 | 2-methoxymethyl-6-methyl-4-(nonafluorobut-2-yl)phenyl | 2.06 | 657(+) | 2 |
| A10 | — | 0 | 2-chloro-6-methylthio-4-(nonafluorobut-2-yl)phenyl | 2.12 | 677(−) | 2 |
| A11 | — | 0 | 2-methoxy-6-methyl-4-(nonafluorobut-2-yl)phenyl | 2.11 | 643(+) | 1 |
| A12 | — | 0 | 2-bromo-6-chloro-4-(hexafluoro-2-benzoyloxyprop-2-yl)phenyl 9.08 (s, 1H), 8.11 (m, 3H), 7.78 (s, 1H), 7.88 (m, 1H), 7.82 (m, 1H), 7.52-7.75 (m, 8H), 2.60 (s, 3H) | — | — | |
| A13 | — | 0 | 2-bromo-6-chloro-4-(hexafluoro-2-hydroxyprop-2-yl)phenyl 9.09 (s, 1H), 8.08 (s, 1H), 7.95 (s, 1H), 7.82-7.93 (m, 4H), 7.62-7.70 (m, 3H), 4.02 (bs, OH), 2.62 (s, 3H) | — | — | |
| A14 | — | 0 | 2,6-dichloro-3-fluoro-4-(heptafluoroprop-2-yl)phenyl | 2.08 | 633(−) | 2 |
| A15 | — | 0 | 2-ethyl-6-methyl-4-(octafluoro-2-hydroxybut-2-yl)phenyl | 1.97 | 639(+) | 2 |
| A16 | — | 0 | 2,6-dimethyl-4-(nonafluorobut-2-yl)phenyl | 2.08 | 625(−) | 2 |
| A17 | — | 0 | 2,6-dimethyl-4-(undecafluorocyclohexyl)phenyl | 2.16 | 689(+) | 2 |
| A18 | 2-F | 1 | 2,6-dichloro-4-(nonafluorobut-2-yl)phenyl | 2.09 | 663(−) | 2 |
| A19 | — | 0 | 2,6-dichloro-4-(1,2,2,2-tetrafluoro-1-trifluoromethylethyl)phenyl | 2.04 | 615(−) | 3 |
| A20 | — | 0 | 2-bromo,6-chloro-4-(1,2,2,2-tetrafluoro-1-trifluoromethylethyl)phenyl 9.08 (s, 1H), 8.24 (sb, 1H), 8.15 (sb, 1H), 7.92-7.82 (m, 3H), 7.74 (s, 1H), 7.68 (m, 1H), 7.62 (m, 2H), 2.59 (s, 3H) | — | — | |

Biological Examples

These Examples illustrate the insecticidal and acaricidal properties of the compounds of formula (I). The tests were performed as follows:

Spodoptera Littoralis (Egyptian Cotton Leafworm):
Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).
The following compound gave at least 80% control of *Spodoptera littoralis*: A1, A2, A3, A4, A5, A6, A7, A8, A9, A10, A11, A12, A14, A15, A16, A17, A18, A19, A20.

Heliothis Virescens (Tobacco Budworm):
Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.
The following compound gave at least 80% control of *Heliothis virescens*: A1, A2, A3, A4, A5, A6, A7, A8, A9, A10, A11, A12, A14, A15, A16, A17, A18, A19, A20.

Plutella Xylostella (Diamond Back Moth):
24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.
The following compound gave at least 80% control of *Plutella xylostella*: A1, A2, A3, A4, A5, A6, A7, A8, A9, A10, A11, A12, A13, A14, A15, A16, A17, A18, A19, A20.

Diabrotica Balteata (Corn Root Worm):
A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.
The following compound gave at least 80% control of *Diabrotica balteata*: A1, A2, A3, A4, A5, A6, A7, A8, A9, A10, A11, A12, A13, A14, A16, A17, A18, A19, A20.

Thrips Tabaci (Onion Thrips):
Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.
The following compounds gave at least 80% control of *Thrips tabaci*: A1, A2, A3, A4, A5, A6, A7, A8, A9, A10, A14, A16, A17, A18, A19, A20.

Tetranychus Urticae (Two-Spotted Spider Mite):
Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.
The following compounds gave at least 80% control of *Tetranychus urticae*: A1, A2, A3, A4, A5, A6, A7, A8, A9, A10, A11, A12, A13, A14, A15, A16, A17, A19, A20.

The comparative data between the compounds having a 2-methyl-4-cyano phenyl and compounds having a 2-methyl phenyl or a 4-cyano phenyl demonstrate that compounds having a 2-methyl-4-cyano phenyl have unexpectedly greater insecticidal activity.

The invention claimed is:
1. A compound of formula (I):

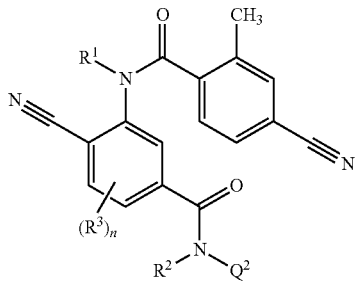

wherein
R$^1$ is hydrogen, C$_1$-C$_8$alkyl, C$_1$-C$_8$alkylcarbonyl, or C$_1$-C$_8$alkoxycarbonyl;
R$^2$ is hydrogen, C$_1$-C$_8$alkyl, C$_1$-C$_8$alkylcarbonyl, or C$_1$-C$_8$alkoxycarbonyl;
each R$^3$ is independently halogen;
n is 0, 1, 2 or 3;
Q$^2$ is a group of formula (II):

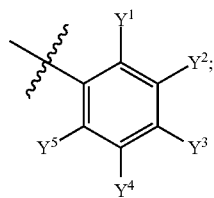

Y$^1$ and Y$^5$ are each independently selected from halogen, cyano, C$_1$-C$_4$alkyl, C$_1$-C$_4$haloalkyl, C$_1$-C$_4$alkoxy, C$_1$-C$_4$haloalkoxy, C$_1$-C$_4$alkoxy-C$_1$-C$_4$alkyl, C$_1$-C$_3$alkylthio, C$_1$-C$_3$haloalkylthio, C$_1$-C$_3$alkylsulfinyl, C$_1$-C$_3$haloalkylsulfinyl, C$_1$-C$_3$alkylsulfonyl and C$_1$-C$_3$haloalkylsulfonyl;
Y$^3$ is selected from C$_2$-C$_6$perfluoroalkyl, C$_2$-C$_6$perfluorocycloalkyl, hydroxy-C$_2$-C$_6$perfluoroalkyl, C$_1$-C$_4$alkylcarbonyloxy-C$_2$-C$_6$perfluoroalkyl, C$_1$-C$_4$haloalkylcarbonyloxy-C$_2$-C$_6$perfluoroalkyl, C$_1$-C$_6$perfluoroalkylthio, C$_1$-C$_6$perfluoroalkylsulfinyl, C$_1$-C$_{1-6}$perfluoroalkylsulfonyl, arylcarbonyloxy-C$_2$-C$_6$perfluoroalkyl and arylcarbonyloxy-C$_2$-C$_6$perfluoroalkyl in which the aryl group may be substituted by one to five R$^4$ groups, which may be the same or different;
Y$^2$ and Y$^4$ are each independently selected from hydrogen, halogen and C$_1$-C$_4$alkyl; and
each R$^4$ is independently selected from halogen, cyano, nitro, C$_1$-C$_4$alkyl, C$_1$-C$_4$haloalkyl, C$_1$-C$_4$alkoxy or C$_1$-C$_4$haloalkoxy;
or an agrochemically acceptable salt or N-oxide thereof.
2. A compound according to claim 1 wherein R$^1$ and R$^2$ are both hydrogen.
3. A compound according to claim 1 wherein R$^3$ is fluoro.
4. A compound according to claim 1 wherein n is 0 or 1.
5. A compound according to claim 1 wherein Y$^1$ and Y$^5$ are each independently selected from fluoro, chloro, bromo, cyano, methyl, ethyl, methoxy, methylthio, and methoxymethyl.

6. A compound according to claim 1 wherein Y$^2$ and Y$^4$ are each independently selected from hydrogen, chloro, fluoro and methyl.
7. A compound according to claim 1 wherein Y$^3$ is heptafluoropropyl, nonafluorobutyl, undecafluorocyclohexyl, heptafluoropropylthio, heptafluoropropylsulfinyl, or heptafluoropropylsulfonyl.
8. A compound according to claim 1 wherein Q$^2$ is selected from
2-bromo-6-chloro-4-(hexafluoro-2-benzoyloxyprop-2-yl)phenyl,
2-bromo-6-chloro-4-(hexafluoro-2-hydroxyprop-2-yl)phenyl,
2-bromo-6-chloro-4-(nonafluorobut-2-yl)phenyl,
2-bromo-6-ethyl-4-(nonafluorobut-2-yl)phenyl,
2-chloro-6-cyano-4-(nonafluorobut-2-yl)phenyl,
2-chloro-6-methylthio-4-(nonafluorobut-2-yl)phenyl,
2,6-dibromo-4-(heptafluoroprop-2-yl)phenyl,
2,6-dibromo-4-(nonafluorobut-2-yl)phenyl,
2,6-dichloro-3-fluoro-4-(heptafluoroprop-2-yl)phenyl,
2,6-dichloro-4-(nonafluorobut-2-yl)phenyl,
2,6-dimethyl-4-(nonafluorobut-2-yl)phenyl,
2,6-dimethyl-4-(undecafluorocyclohexyl)phenyl,
2-ethyl-6-methyl-4-(nonafluorobut-2-yl)phenyl,
2-ethyl-6-methyl-4-(octafluoro-2-hydroxybut-2-yl)phenyl,
2-methoxymethyl-6-methyl-4-(nonafluorobut-2-yl)phenyl, and
2-methoxy-6-methyl-4-(nonafluorobut-2-yl)phenyl.
9. A compound according to claim 1, which is selected from
4-cyano-3-(4'-cyano-2'-methyl-benzoylamino)-N-[2,6-dibromo-4-(1,2,2,3,3,3-hexafluoro-1-trifluoromethyl-propyl)-phenyl]-benzamide;
4-cyano-3-(4'-cyano-2'-methylbenzoylamino)-N-[2,6-dichloro-4-(1,2,2,3,3,3-hexafluoro-1-trifluoromethyl-propyl)phenyl]-2-fluorobenzamide;
N-[2-chloro-6-cyano-4-(1,2,2,3,3,3-hexafluoro-1-trifluoromethylpropyl)phenyl]-4-cyano-3-(4'-cyano-2'-methylbenzoylamino)benzamide;
N-[2-bromo-6-chloro-4-[1,1,1,3,3,3-hexafluoropropan-2-ol)phenyl]-4-cyano-3-(4'-cyano-2'-methylbenzoylamino)benzamide;
N-[2-bromo-6-chloro-4-(1,2,2,3,3,3-hexafluoro-1-trifluoromethylpropyl)phenyl]-4-cyano-3-(4'-cyano-2'-methylbenzoylamino)benzamide;
4-cyano-3-(4'-cyano-2'-methylbenzoylamino)-N-[2,6-dichloro-4-(1,2,2,3,3,3-hexafluoro-1-trifluoromethylpropyl)phenyl]benzamide;
4-cyano-3-(4'-cyano-2'-methylbenzoylamino)-N-[2,6-dichloro-4-(1,2,2,2-tetrafluoro-1-trifluoromethylethyl)phenyl]benzamide; and
4-cyano-3-(4'-cyano-2'-methylbenzoylamino)-N-[2-bromo-6-chloro-4-(1,2,2,2-tetrafluoro-1-trifluoromethylethyl)phenyl]benzamide.
10. A method of controlling insects, acarines, nematodes or molluscs which comprises applying to a pest, to a locus of a pest, or to a plant susceptible to attack by a pest a compound of claim 1.
11. An insecticidal, acaricidal, nematicidal or molluscicidal composition comprising a compound of claim 1 together with an agrochemically acceptable diluent or carrier.
12. A composition according to claim 11 which further comprises one or more additional insecticidal, acaricidal, nematicidal or molluscicidal compounds.

* * * * *